United States Patent
Cao et al.

(10) Patent No.: US 11,520,064 B2
(45) Date of Patent: *Dec. 6, 2022

(54) X-RAY DETECTORS CAPABLE OF IDENTIFYING AND MANAGING CHARGE SHARING

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

(*) Notice: Subject to any disclaimer, the term of this patent is extended or adjusted under 35 U.S.C. 154(b) by 55 days.

This patent is subject to a terminal disclaimer.

(21) Appl. No.: 17/175,906

(22) Filed: Feb. 15, 2021

(65) Prior Publication Data

US 2021/0165116 A1  Jun. 3, 2021

Related U.S. Application Data

(63) Continuation of application No. 16/177,646, filed on Nov. 1, 2018, now Pat. No. 10,948,613, which is a continuation of application No. PCT/CN2017/072169, filed on Jan. 23, 2017.

(51) Int. Cl.
| | |
|---|---|
| *G01T 1/24* | (2006.01) |
| *G01T 1/29* | (2006.01) |
| *A61B 6/00* | (2006.01) |
| *G01N 23/083* | (2018.01) |

(52) U.S. Cl.
CPC ............ *G01T 1/247* (2013.01); *A61B 6/4233* (2013.01); *G01N 23/083* (2013.01); *G01T 1/2928* (2013.01)

(58) Field of Classification Search
CPC ...... A61B 6/4233; G01T 1/247; G01T 1/2928
See application file for complete search history.

(56) References Cited

U.S. PATENT DOCUMENTS

| | | | |
|---|---|---|---|
| 6,232,607 B1 | 5/2001 | Huang | |
| 10,948,613 B2* | 3/2021 | Cao | .......................... G01T 1/247 |
| 2005/0139777 A1 | 6/2005 | Rostaing et al. | |
| 2006/0039532 A1 | 2/2006 | Wu et al. | |
| 2006/0056581 A1* | 3/2006 | Hoffman | ................ A61B 6/032 |
| | | | 378/19 |

(Continued)

FOREIGN PATENT DOCUMENTS

| | | |
|---|---|---|
| CN | 101600974 A | 12/2009 |
| CN | 106249270 A | 12/2016 |

(Continued)

*Primary Examiner* — Chih-Cheng Kao
(74) *Attorney, Agent, or Firm* — IPro, PLLC; Qian Gu

(57) ABSTRACT

An apparatus suitable for detecting X-ray is disclosed. In one example, the apparatus comprises an X-ray absorption layer and a controller. The X-ray absorption layer comprises a first pixel and a second pixel. The controller is configured for determining whether all carriers generated in the X-ray absorption layer by an X-ray photon are collected by the first pixel and the second pixel, and determining the energy of the X-ray photon based on a sum of a first portion of the carriers that is collected by the first pixel and a second portion of the carriers that is collected by the second pixel.

12 Claims, 28 Drawing Sheets

(56) References Cited

U.S. PATENT DOCUMENTS

| | | | |
|---|---|---|---|
| 2006/0086913 A1* | 4/2006 | Spahn | G01T 1/2018 250/580 |
| 2011/0168909 A1 | 7/2011 | Nakao et al. | |
| 2012/0112088 A1* | 5/2012 | Abraham | G01T 1/171 250/336.1 |
| 2012/0161016 A1* | 6/2012 | Schmitt | G01T 1/17 250/370.06 |
| 2013/0100330 A1 | 4/2013 | Yamada et al. | |
| 2015/0369929 A1 | 12/2015 | Durst et al. | |

FOREIGN PATENT DOCUMENTS

| | | |
|---|---|---|
| TW | 201643468 A | 12/2016 |
| WO | 2016161544 A1 | 10/2016 |

\* cited by examiner

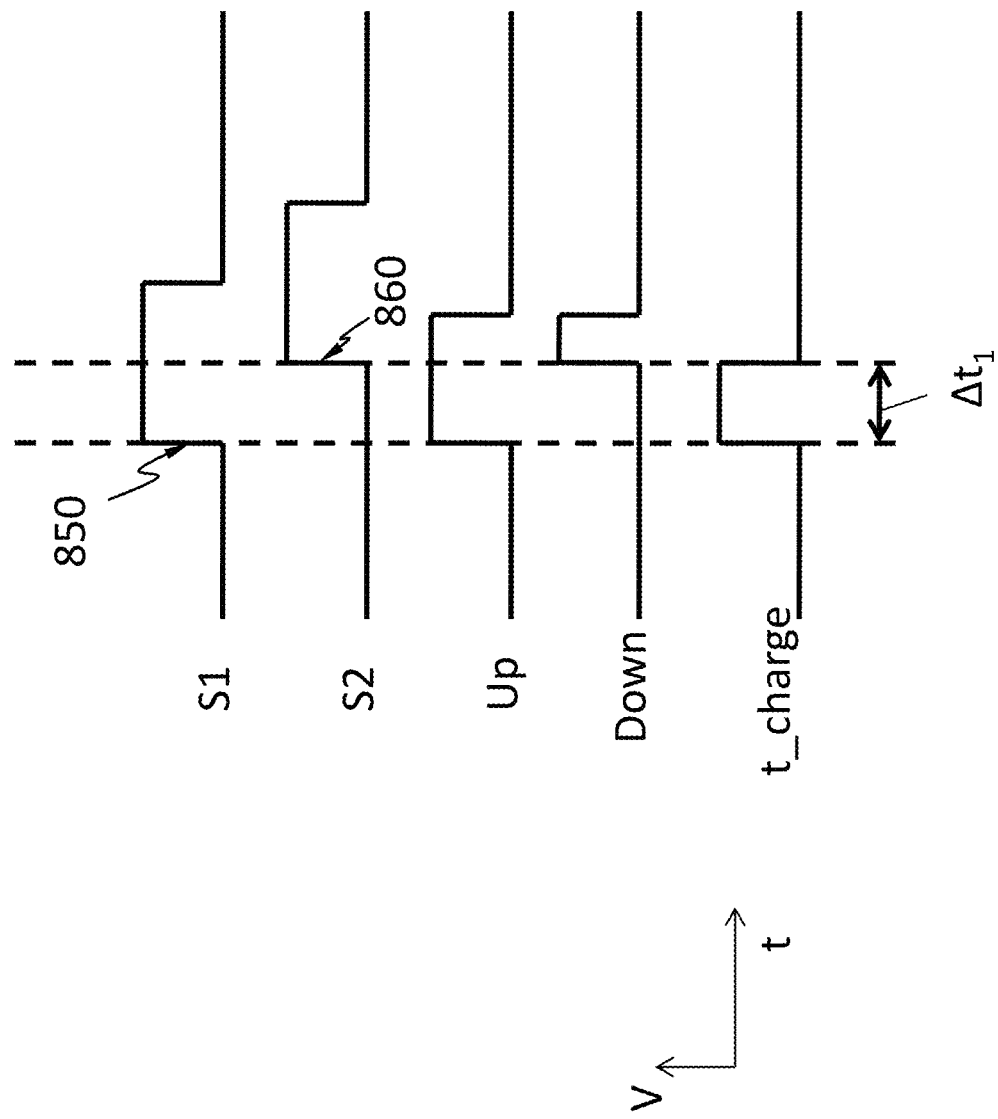

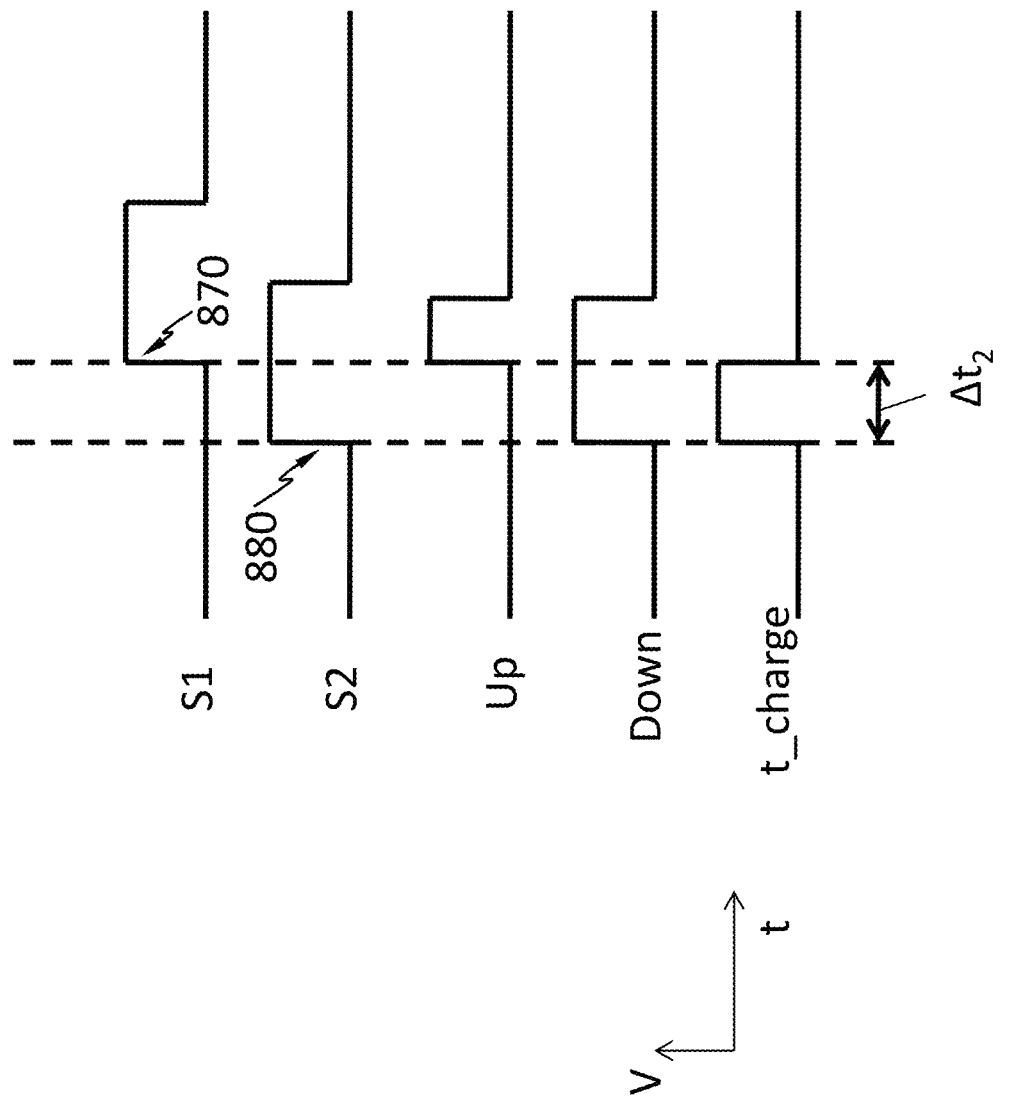

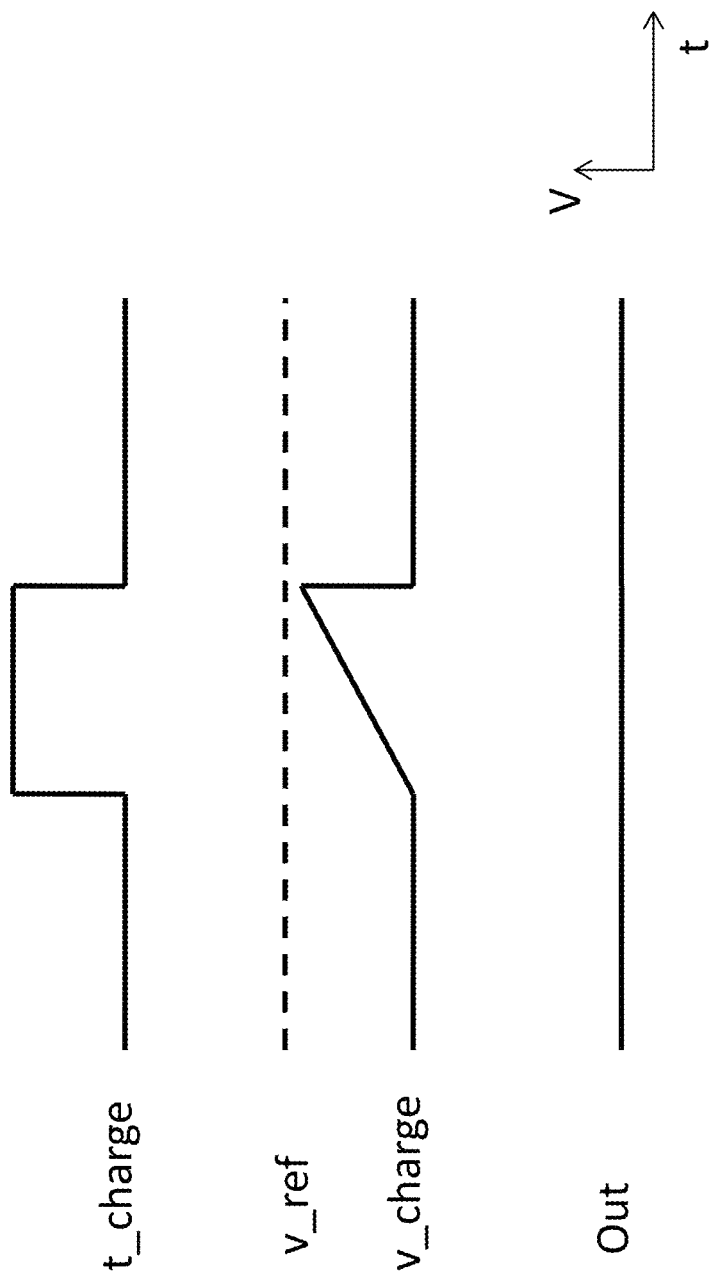

X-RAY DETECTORS CAPABLE OF IDENTIFYING AND MANAGING CHARGE SHARING

TECHNICAL FIELD

The disclosure herein relates to X-ray detectors, particularly relates to X-ray detectors capable of identifying and managing charge sharing.

BACKGROUND

X-ray detectors may be devices used to measure the flux, spatial distribution, spectrum or other properties of X-rays.

X-ray detectors may be used for many applications. One important application is imaging. X-ray imaging is a radiography technique and can be used to reveal the internal structure of a non-uniformly composed and opaque object such as the human body. Another important application is elemental analysis. Elemental analysis is a process where a sample of some material is analyzed for its elemental composition.

Early X-ray detectors include photographic plates and photographic films. A photographic plate may be a glass plate with a coating of light-sensitive emulsion.

In the 1980s, photostimulable phosphor plates (PSP plates) became available. A PSP plate may contain a phosphor material with color centers in its lattice. When the PSP plate is exposed to X-ray, electrons excited by X-ray are trapped in the color centers until they are stimulated by a laser beam scanning over the plate surface. As the plate is scanned by laser, trapped excited electrons give off light, which is collected by a photomultiplier tube. The collected light is converted into a digital image.

Another kind of X-ray detectors are X-ray image intensifiers. In an X-ray image intensifier, X-ray first hits an input phosphor (e.g., cesium iodide) and is converted to visible light. The visible light then hits a photocathode (e.g., a thin metal layer containing cesium and antimony compounds) and causes emission of electrons. The number of emitted electrons is proportional to the intensity of the incident X-ray. The emitted electrons are projected, through electron optics, onto an output phosphor and cause the output phosphor to produce a visible-light image.

Scintillators operate somewhat similarly to X-ray image intensifiers in that scintillators (e.g., sodium iodide) absorb X-ray and emit visible light, which can then be detected by a suitable image sensor for visible light.

Semiconductor X-ray detectors can directly convert X-ray into electric signals and thus offer better performance than previous generations of X-ray detectors. A semiconductor X-ray detector may include a semiconductor layer that absorbs X-ray in wavelengths of interest. When an X-ray photon is absorbed in the semiconductor layer, multiple charge carriers (e.g., electrons and holes) are generated. As used herein, the term "charge carriers," "charges" and "carriers" are used interchangeably. A semiconductor X-ray detector may have multiple pixels that can independently determine the local intensity of X-ray and X-ray photon energy. The charge carriers generated by an X-ray photon may be swept under an electric field into the pixels. If the charge carriers generated by a single X-ray photon are collected by more than one pixel ("charge sharing"), the performance of the semiconductor X-ray detector may be negatively impacted. In applications (e.g., elemental analysis) where X-ray photon energy is determined, charge sharing is especially problematic for accurate photon energy measurement, because the energy of an X-ray photon is determined by the amount of electric charges it generates.

SUMMARY

The teachings disclosed herein relate to methods, systems, and apparatus for X-ray detection. More particularly, the present teaching relates to methods, systems, and apparatus for X-ray detection with charge sharing management.

In one example, an apparatus suitable for detecting X-ray is disclosed. The apparatus comprises an X-ray absorption layer and a controller. The X-ray absorption layer comprises a first pixel and a second pixel. The controller is configured for determining that carriers generated by a first X-ray photon are collected by the first pixel and the second pixel, and resetting signals associated with the carriers collected by the first pixel and the second pixel.

According to an embodiment, the resetting the signals comprises resetting each value of the signals to zero or erasing the signals.

According to an embodiment, the signals associated with the carriers collected by the first pixel and the second pixel comprise a first voltage generated from first carriers collected by the first pixel and a second voltage generated from second carriers collected by the second pixel.

According to an embodiment, the first pixel is associated with a first capacitor charged with the first voltage, and the second pixel is associated with a second capacitor charged with the second voltage.

According to an embodiment, the determining that the carriers generated by the first X-ray photon are collected by the first pixel and the second pixel comprises determining a characteristic associated with the first voltage and the second voltage, and wherein the characteristic is within or greater than a threshold.

According to an embodiment, the characteristic is, or is a function of a time difference between a rising or falling edge of the first voltage and the rising or falling edge of the second voltage.

According to an embodiment, the controller is further configured for: determining that all carriers generated by a second X-ray photon are collected by the first pixel or the second pixel, and determining the energy of the second X-ray photon based on all the carriers generated by the second X-ray photon.

According to an embodiment, the apparatus further comprises a counter configured for registering a number of X-ray photons absorbed by the X-ray absorption layer. The controller is configured for causing the number registered by the counter to increase by one, if the energy of the second X-ray photon equals to or exceeds a predetermined energy threshold.

According to an embodiment, the energy of the second X-ray photon is determined based on a voltage generated from all the carriers generated by the second X-ray photon.

According to an embodiment, the apparatus comprises an array of pixels.

According to an embodiment, the controller comprises a first D-type flip-flop (DFF) and a second DFF, and wherein a first waveform of voltage associated with the first pixel is inputted to the first DFF, and a second waveform of voltage associated with the second pixel is inputted to the second DFF.

According to an embodiment, the controller is further configured to generate a first signal based on a first output signal from the first DFF and a second output signal from the second DFF, and wherein the first signal indicates a time difference of a rising edge or falling edge of the first waveform of voltage and a rising edge or falling edge of the second waveform of voltage.

According to an embodiment, a signal generated based on the first output signal and the second output signal is fed back as an input to the first DFF and the second DFF.

According to an embodiment, the controller further comprises an N-channel field effect transistor (N-FET), a P-channel field effect transistor (P-FET), and a capacitor.

According to an embodiment, the controller is further configured to generate a second signal based on the first signal, and wherein a peak value of the second signal is proportional to the time difference of the rising edge or falling edge of the first waveform of voltage and the rising edge or falling edge of the second waveform of voltage.

Disclosed herein is a system comprising the apparatus described above and an X-ray source. The system is configured for performing X-ray radiography on human chest or abdomen.

Disclosed herein is a system comprising the apparatus described above and an X-ray source. The system is configured for performing X-ray radiography on human mouth.

Disclosed herein is a cargo scanning or non-intrusive inspection (NII) system, comprising the apparatus described above and an X-ray source. The cargo scanning or non-intrusive inspection (NII) system is configured for forming an image based on backscattered X-ray.

Disclosed herein is a cargo scanning or non-intrusive inspection (NII) system, comprising the apparatus described above and an X-ray source. The cargo scanning or non-intrusive inspection (NII) system is configured to form an image using X-ray transmitted through an object inspected.

Disclosed herein is a full-body scanner system comprising the apparatus described above and an X-ray source.

Disclosed herein is an X-ray computed tomography (CT) system comprising the apparatus described above and an X-ray source.

Disclosed herein is an electron microscope comprising the apparatus described above, an electron source and an electronic optical system.

Disclosed herein is a system comprising the apparatus described above. The system is configured for measuring dose of an X-ray source.

Disclosed herein is a system comprising the apparatus described above. The system is an X-ray telescope, or an X-ray microscopy, or a system configured to perform mammography, industrial defect detection, microradiography, casting inspection, weld inspection, or digital subtraction angiography.

In another example, a method is disclosed. The method comprises: determining that carriers generated by a first X-ray photon are collected by a first pixel and a second pixel; and resetting signals associated with the carriers collected by the first pixel and the second pixel.

According to an embodiment, the resetting the signals comprises resetting each value of the signals to zero or erasing the signals.

According to an embodiment, the signals associated with the carriers collected by the first pixel and the second pixel comprise a first voltage generated from first carriers collected by the first pixel and a second voltage generated from second carriers collected by the second pixel.

According to an embodiment, the first pixel is associated with a first capacitor charged with the first voltage, and the second pixel is associated with a second capacitor charged with the second voltage.

According to an embodiment, the determining that the carriers generated by the first X-ray photon are collected by the first pixel and the second pixel comprises determining a characteristic associated with the first voltage and the second voltage, and wherein the characteristic is within or greater than a threshold.

Accordingly to an embodiment, the characteristic is, or is a function of a time difference between a rising or falling edge of the first voltage and the rising or falling edge of the second voltage.

According to an embodiment, the method further comprises: determining that all carriers generated by a second X-ray photon are collected by the first pixel or the second pixel; and determining the energy of the second X-ray photon based on all the carriers generated by the second X-ray photon.

According to an embodiment, the method further comprises: registering a number of X-ray photons absorbed by the X-ray absorption layer; and causing the number registered by the counter to increase by one, if the energy of the second X-ray photon equals to or exceeds a predetermined energy threshold.

According to an embodiment, the energy of the second X-ray photon is determined based on a voltage generated from all the carriers generated by the second X-ray photon.

Disclosed herein is a system suitable for phase-contrast X-ray imaging (PCI), the system comprising: The apparatus described above, a second X-ray detector, and a spacer. The apparatus and the second X-ray detector are spaced apart by the spacer.

According to an embodiment, the apparatus and the second X-ray detector are configured to respectively capture an image of an object simultaneously.

According to an embodiment, the second X-ray detector is identical to the apparatus.

Disclosed herein is a system suitable for phase-contrast X-ray imaging (PCI), the system comprising the apparatus described above. The apparatus is configured to move to and capture images of an object exposed to incident X-ray at different distances from the object.

Figure 3A:
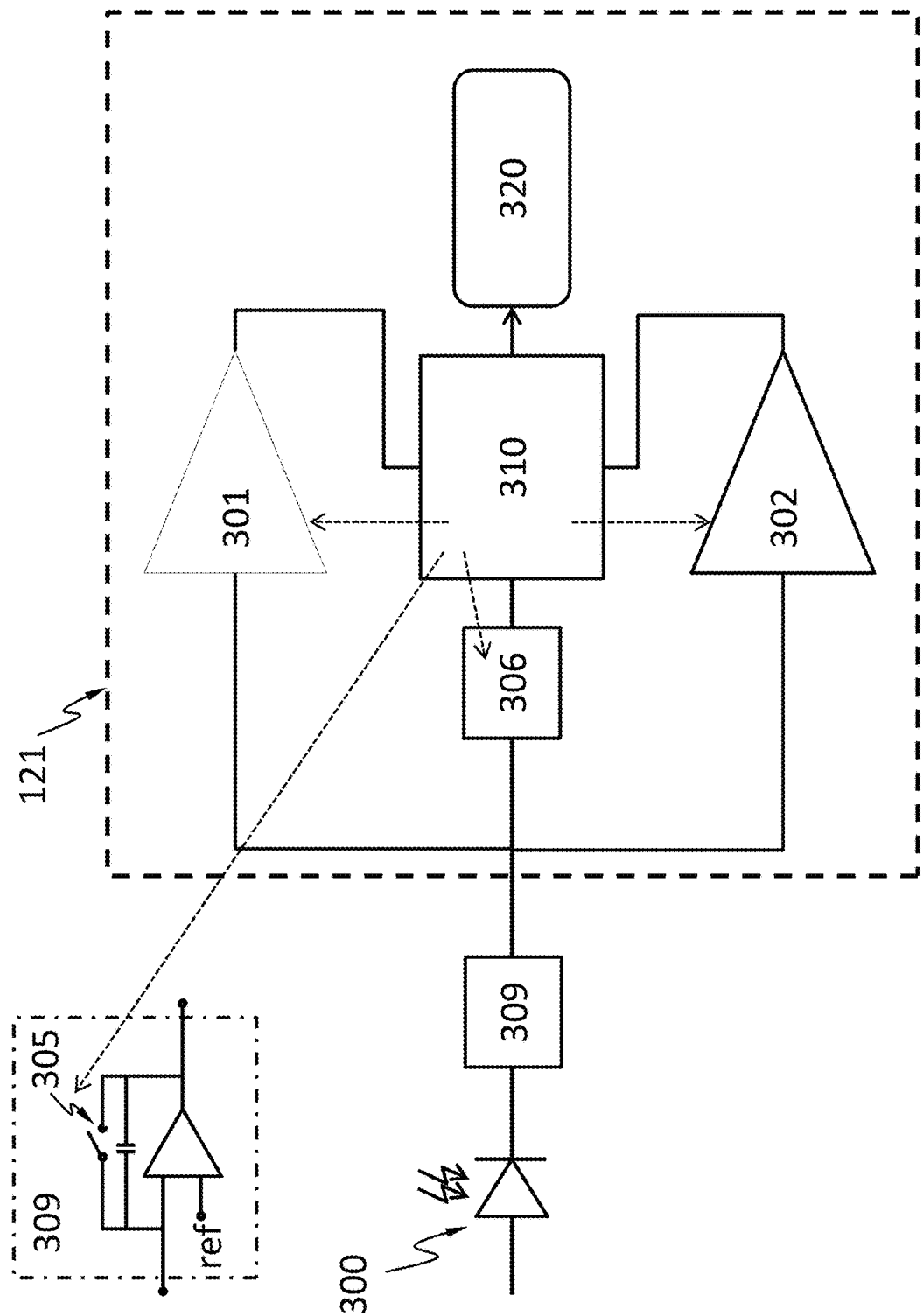
FIG. 3A and FIG. 3B each show a component diagram of an electronic system of the detector in FIG. 1A or FIG. 1B, according to an embodiment.
Figure 3B:
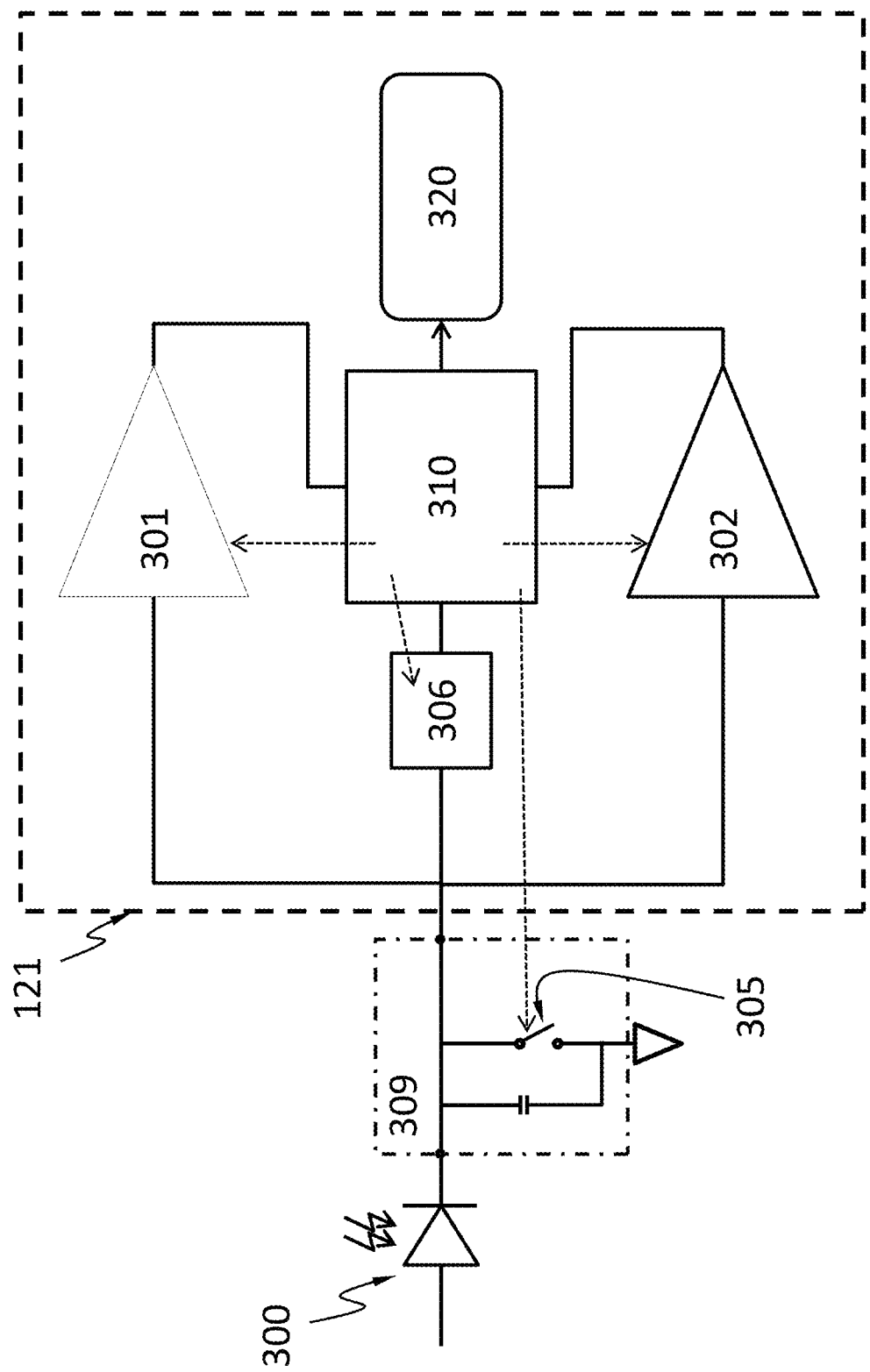
Figure 4:
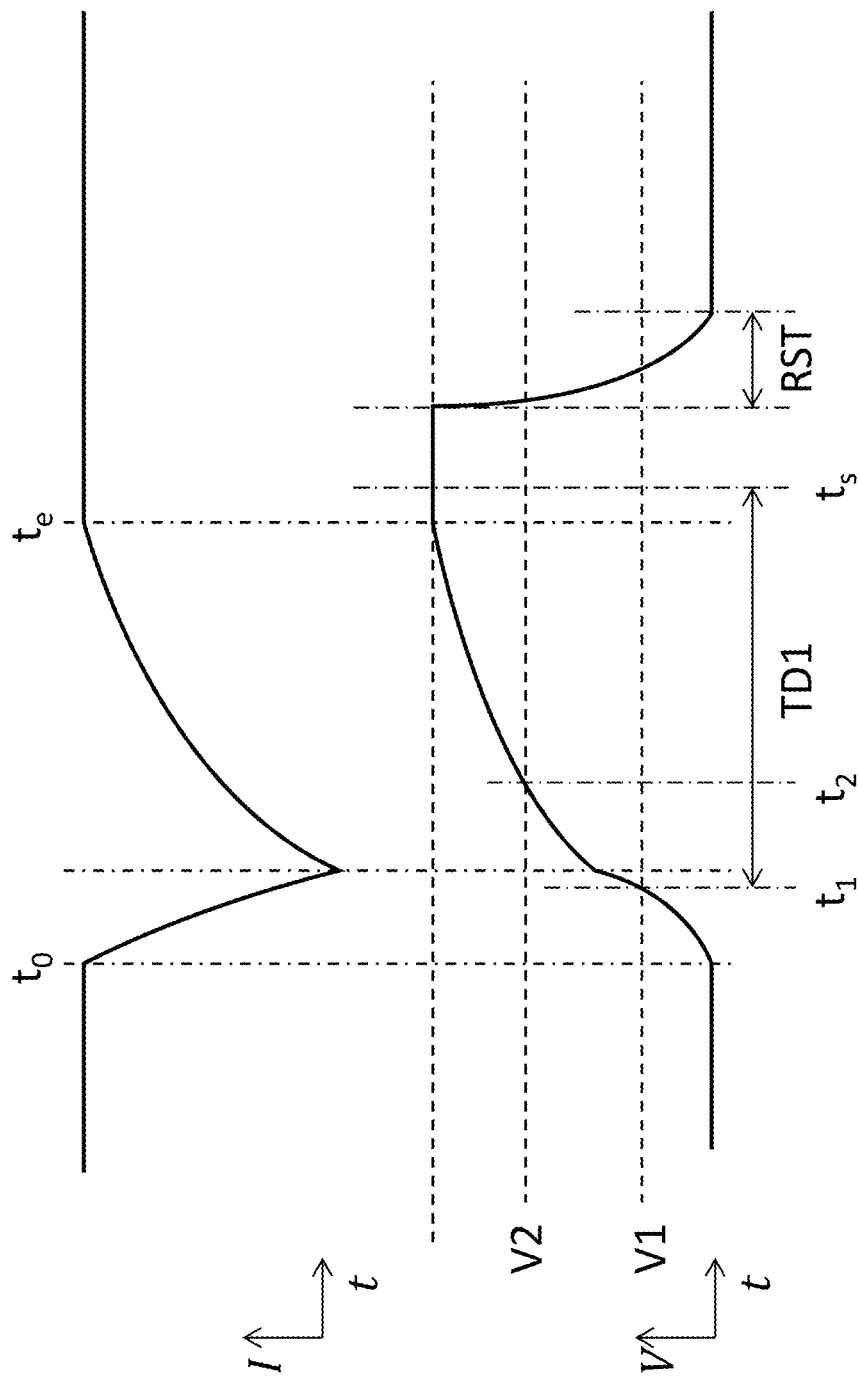
FIG. 4 schematically shows a temporal change of the electric current flowing through an electrode (upper curve) of a diode or an electrical contact of a resistor of an X-ray absorption layer exposed to X-ray, the electric current caused by charge carriers generated by an X-ray photon incident on the X-ray absorption layer, and a corresponding temporal change of the voltage of the electrode (lower curve), according to an embodiment.
Figure 6:
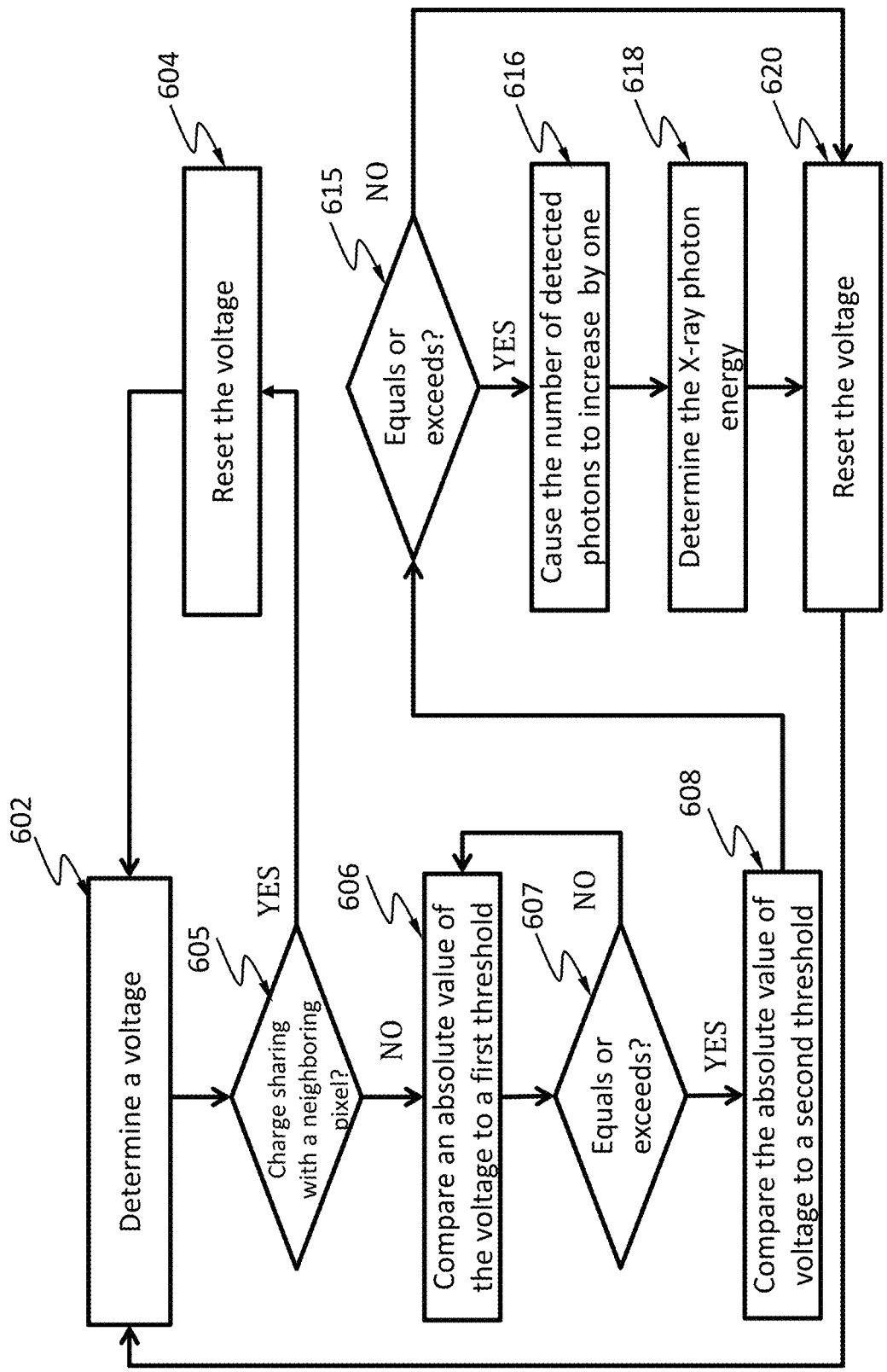
Figure 7:
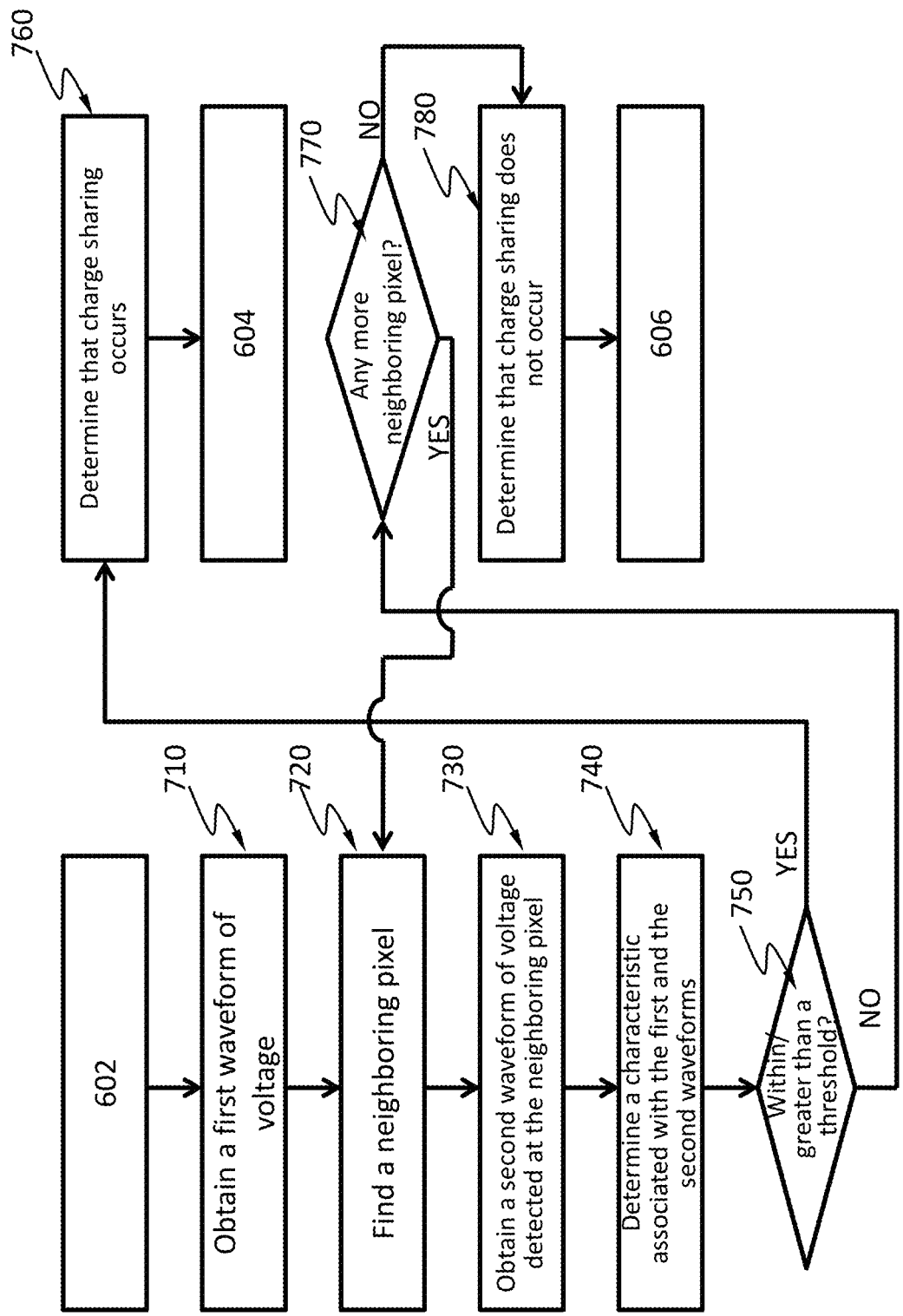
Figure 8A:
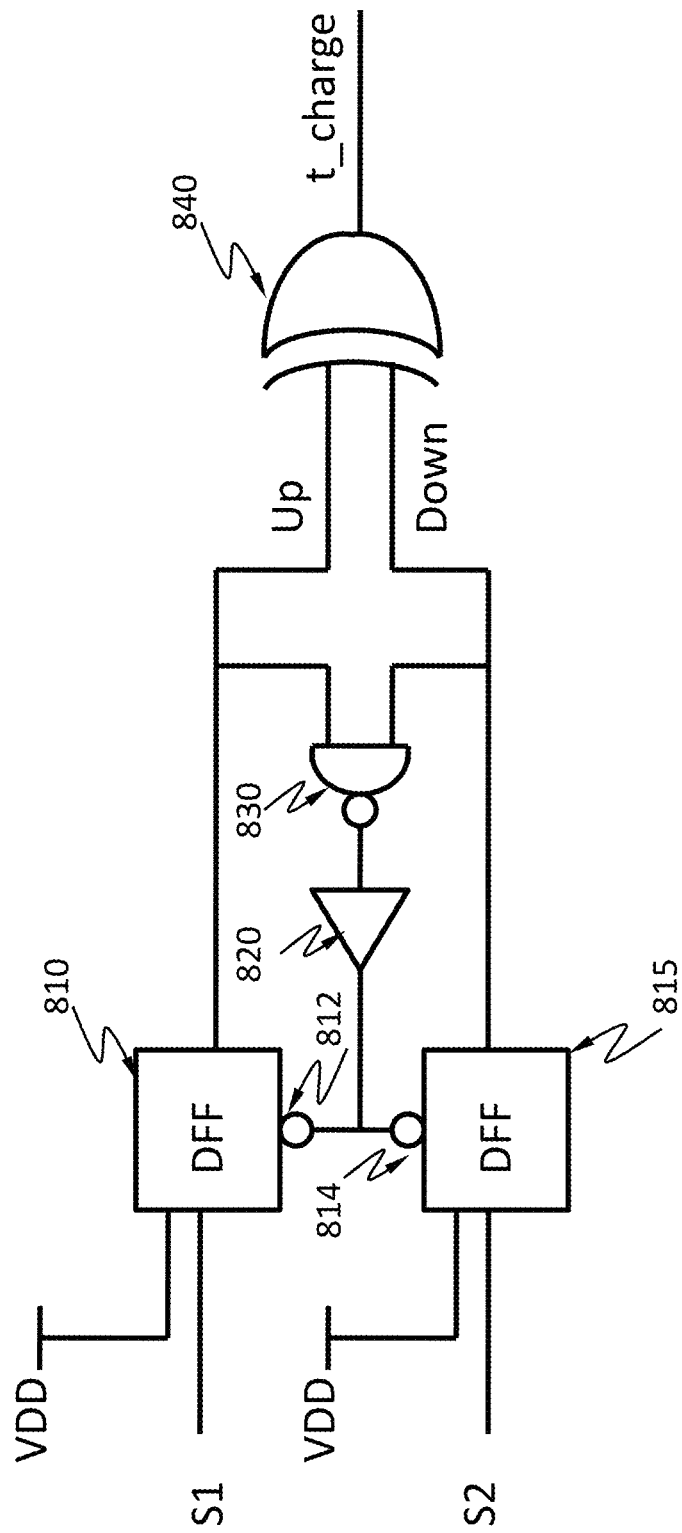
Figure 9A:
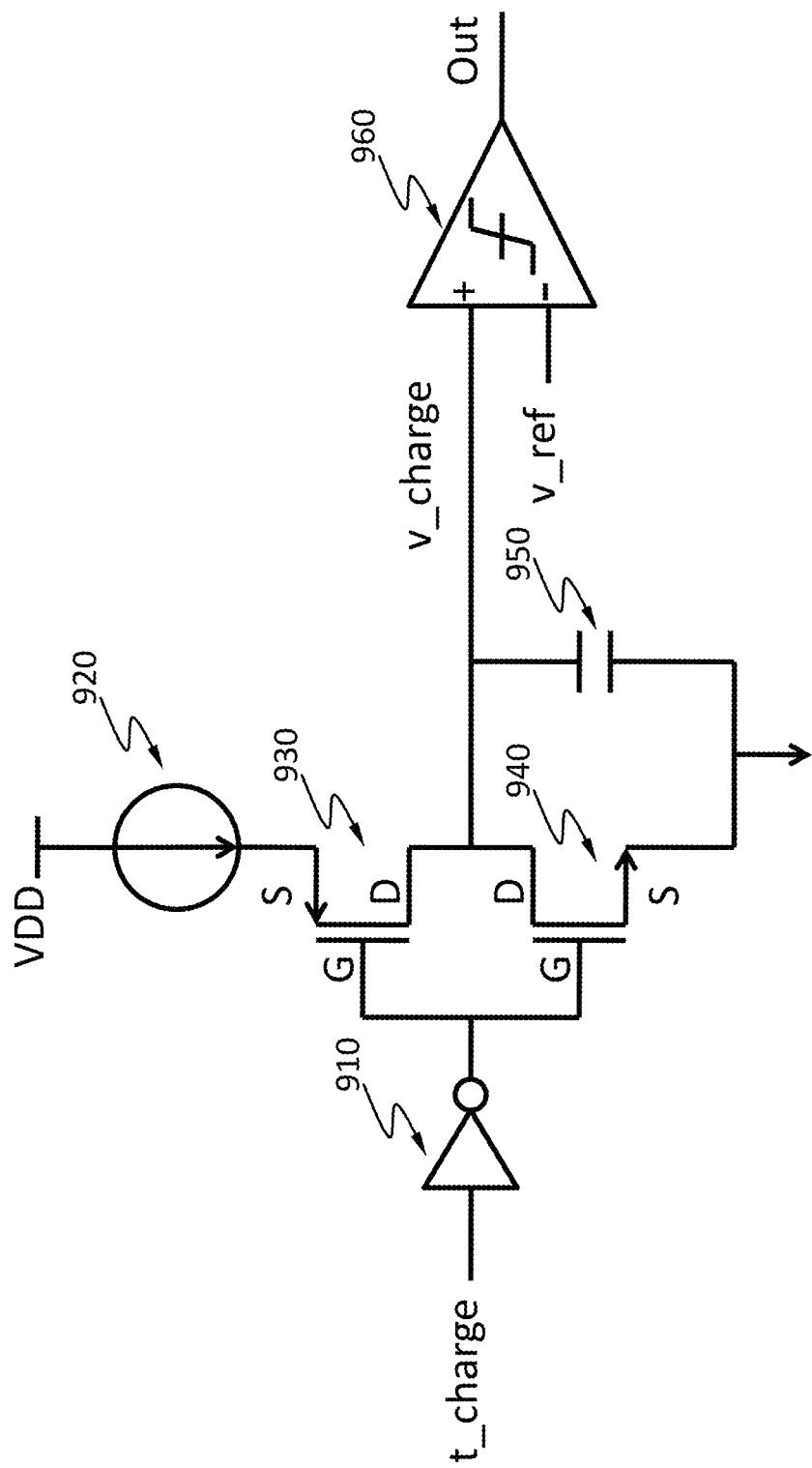
Figure 9B:
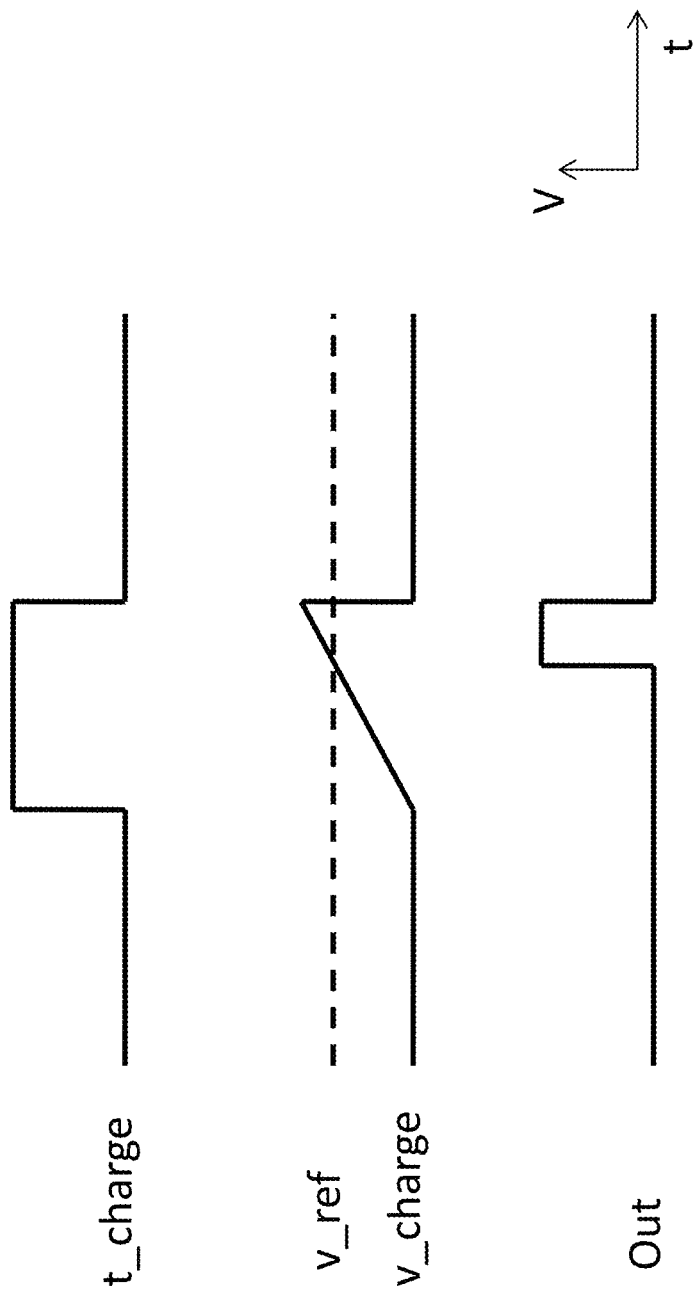
Figure 10:
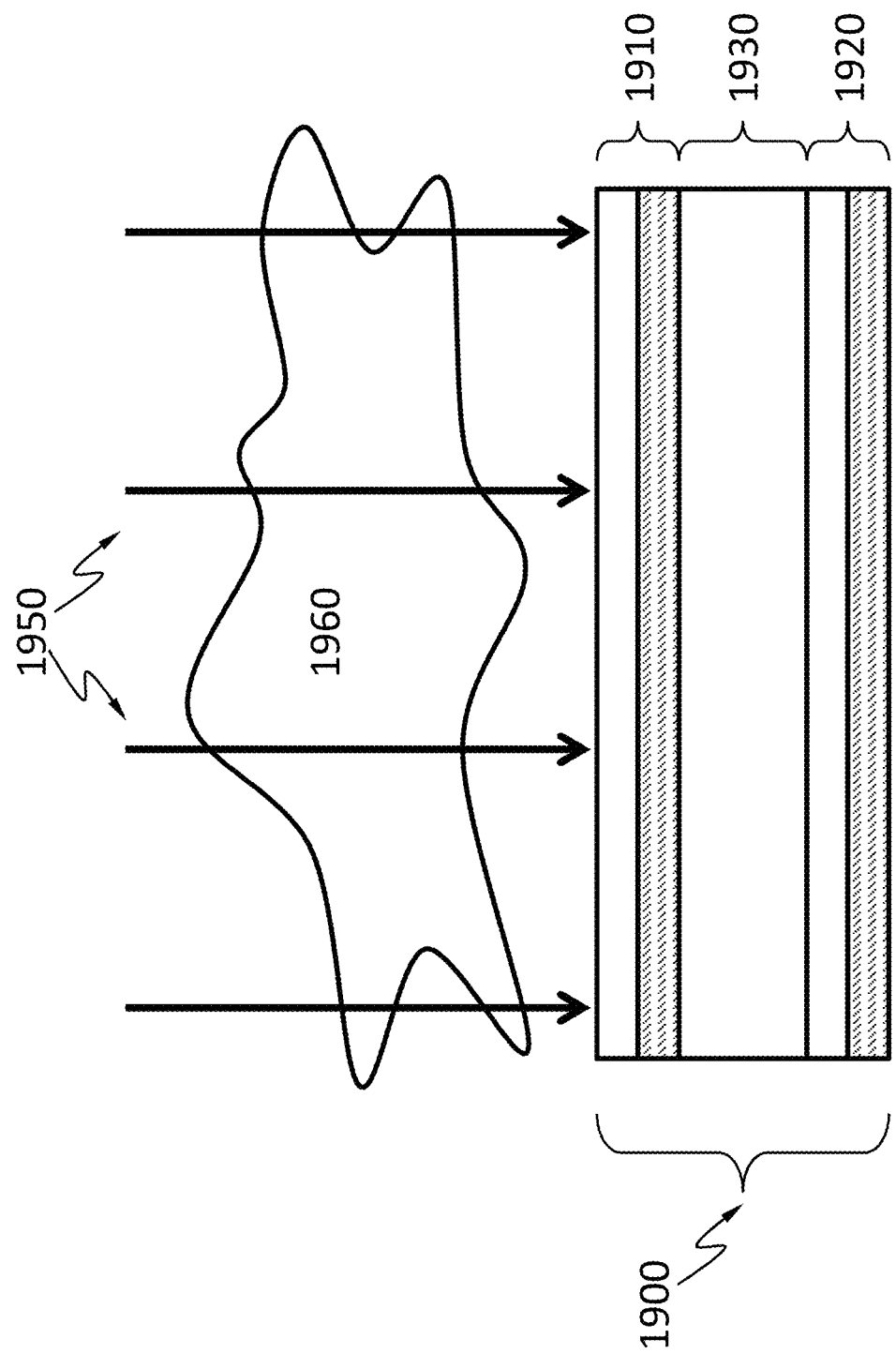
Figure 11:
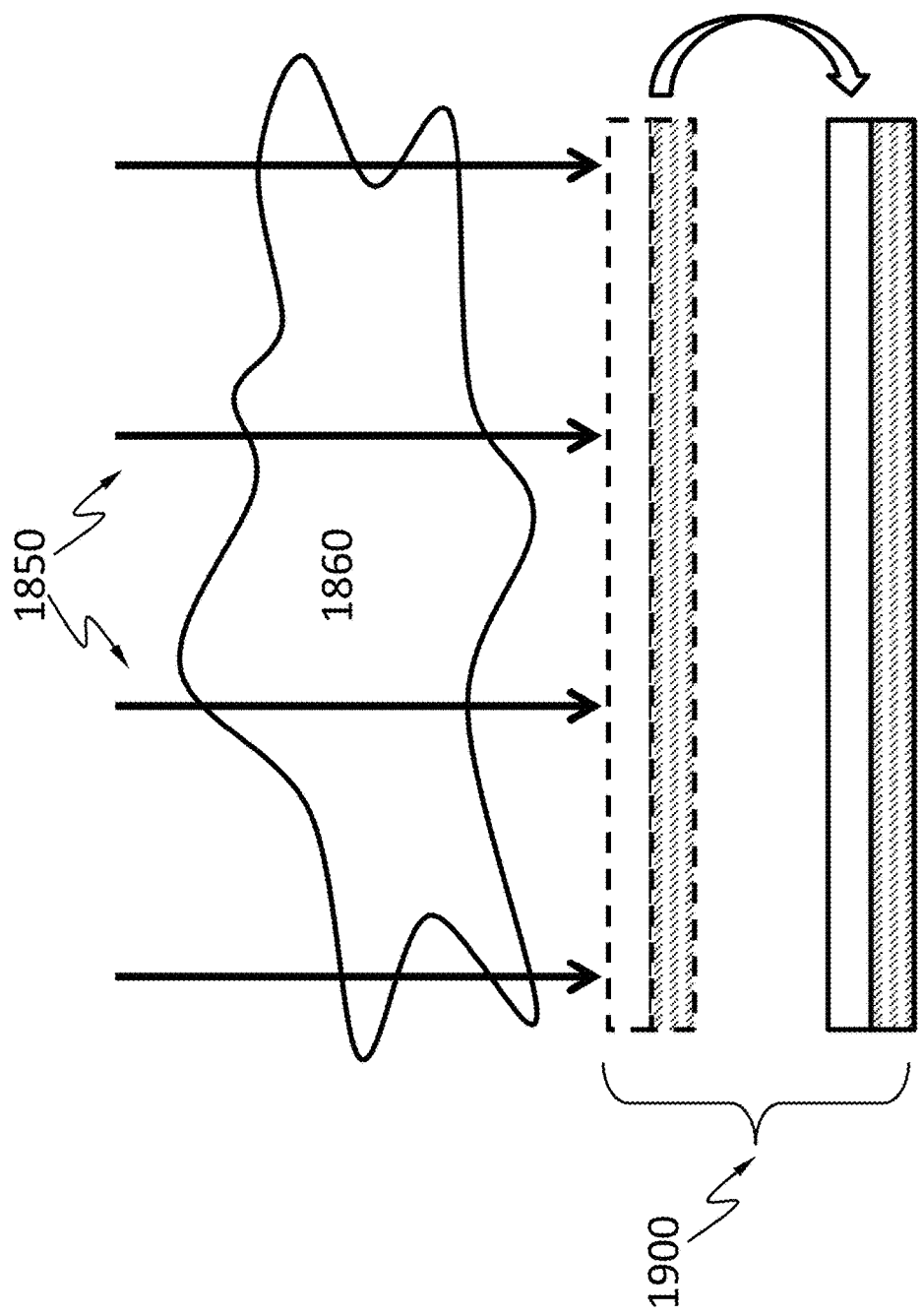
Figure 12:
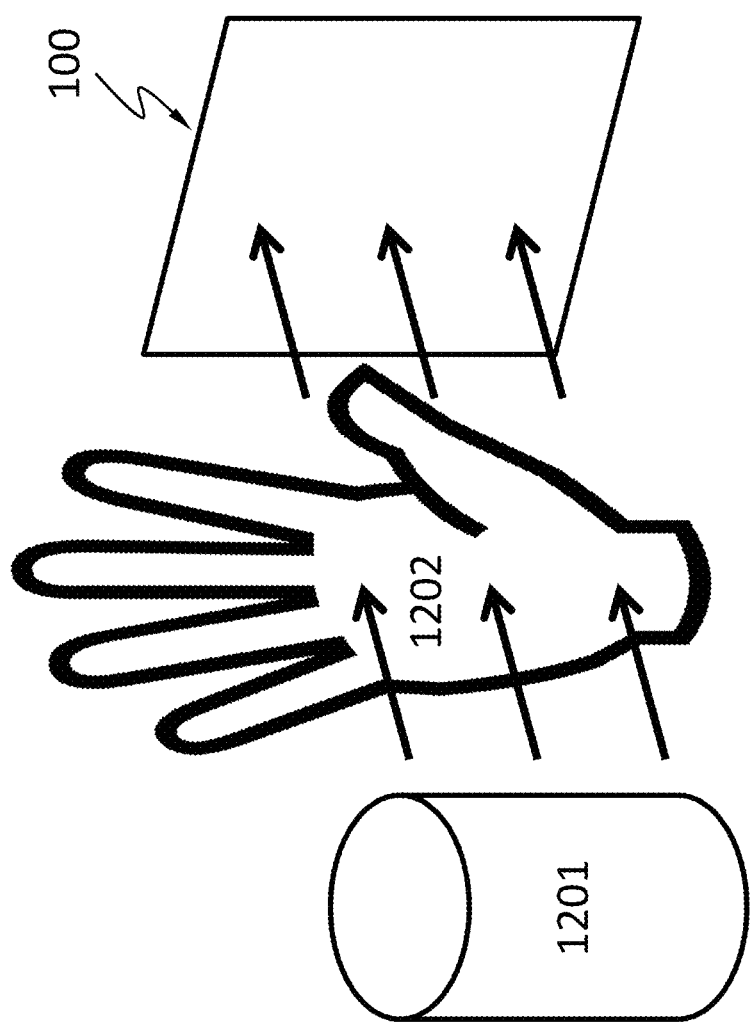
Figure 13:
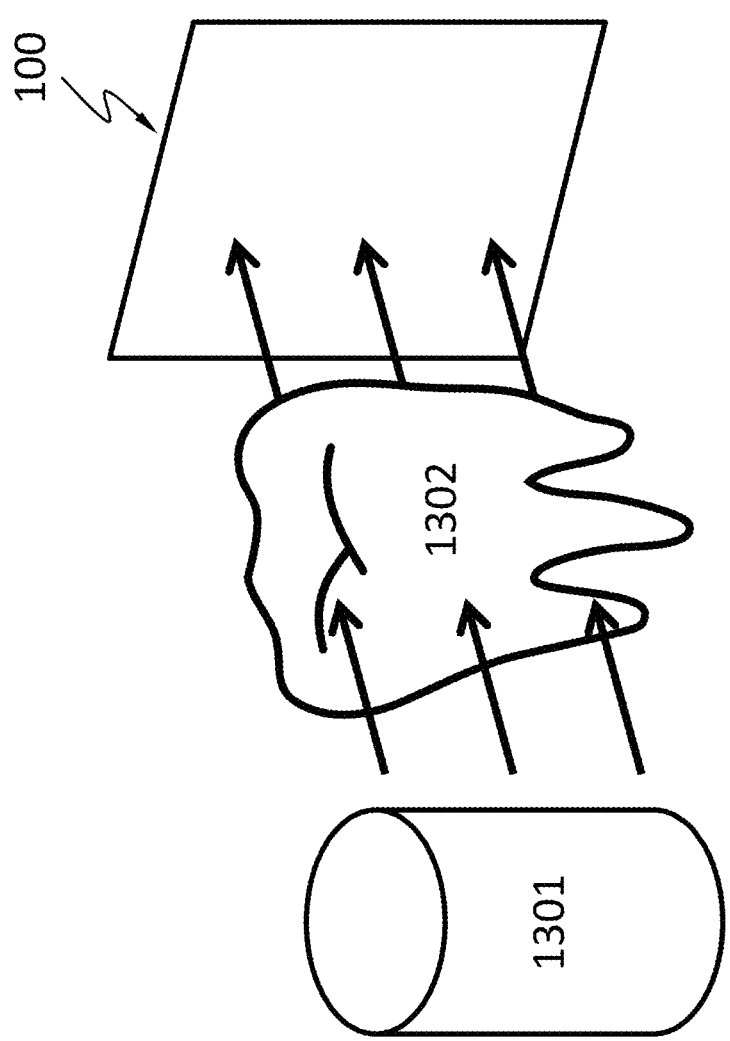
Figure 14:
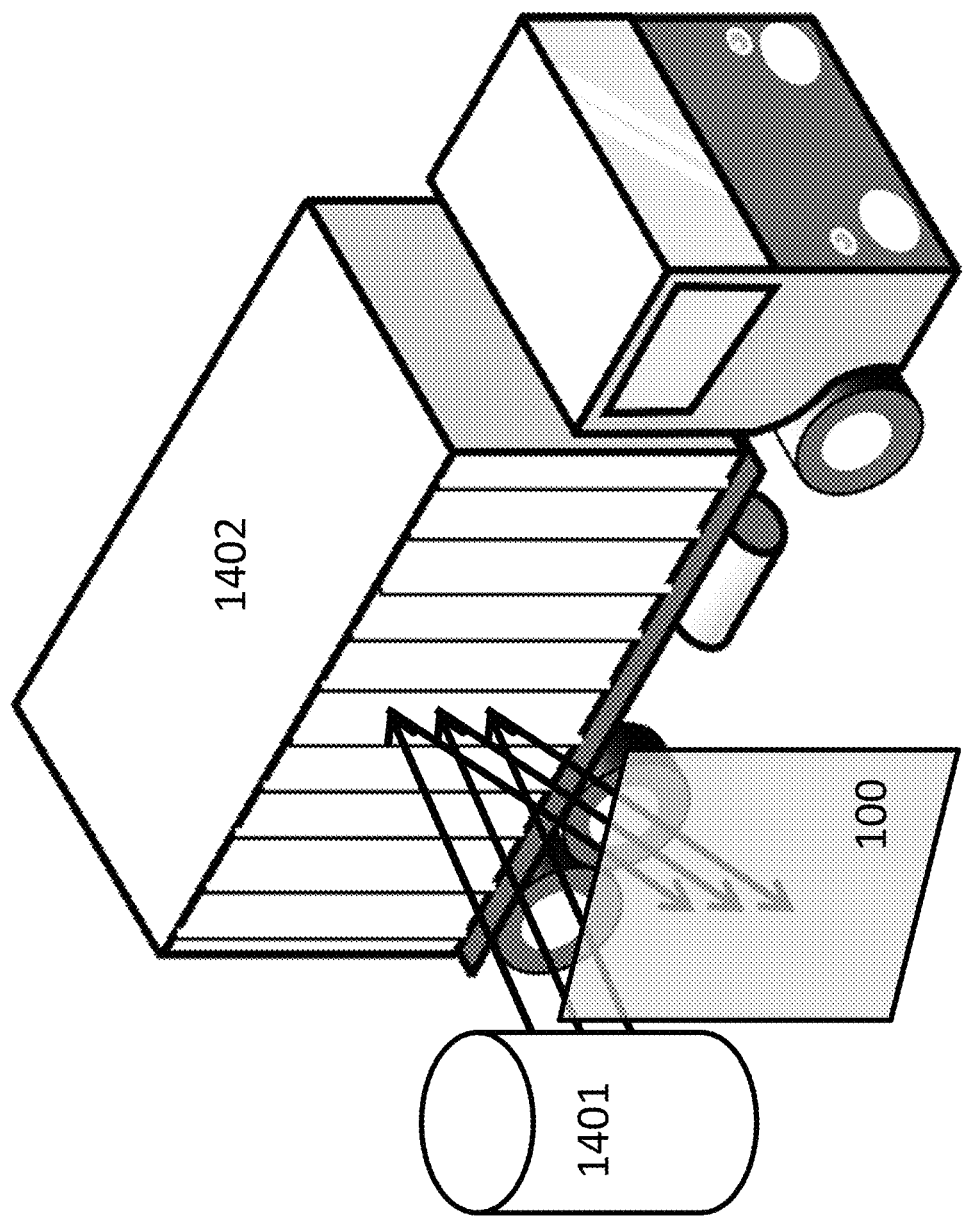
Figure 15:
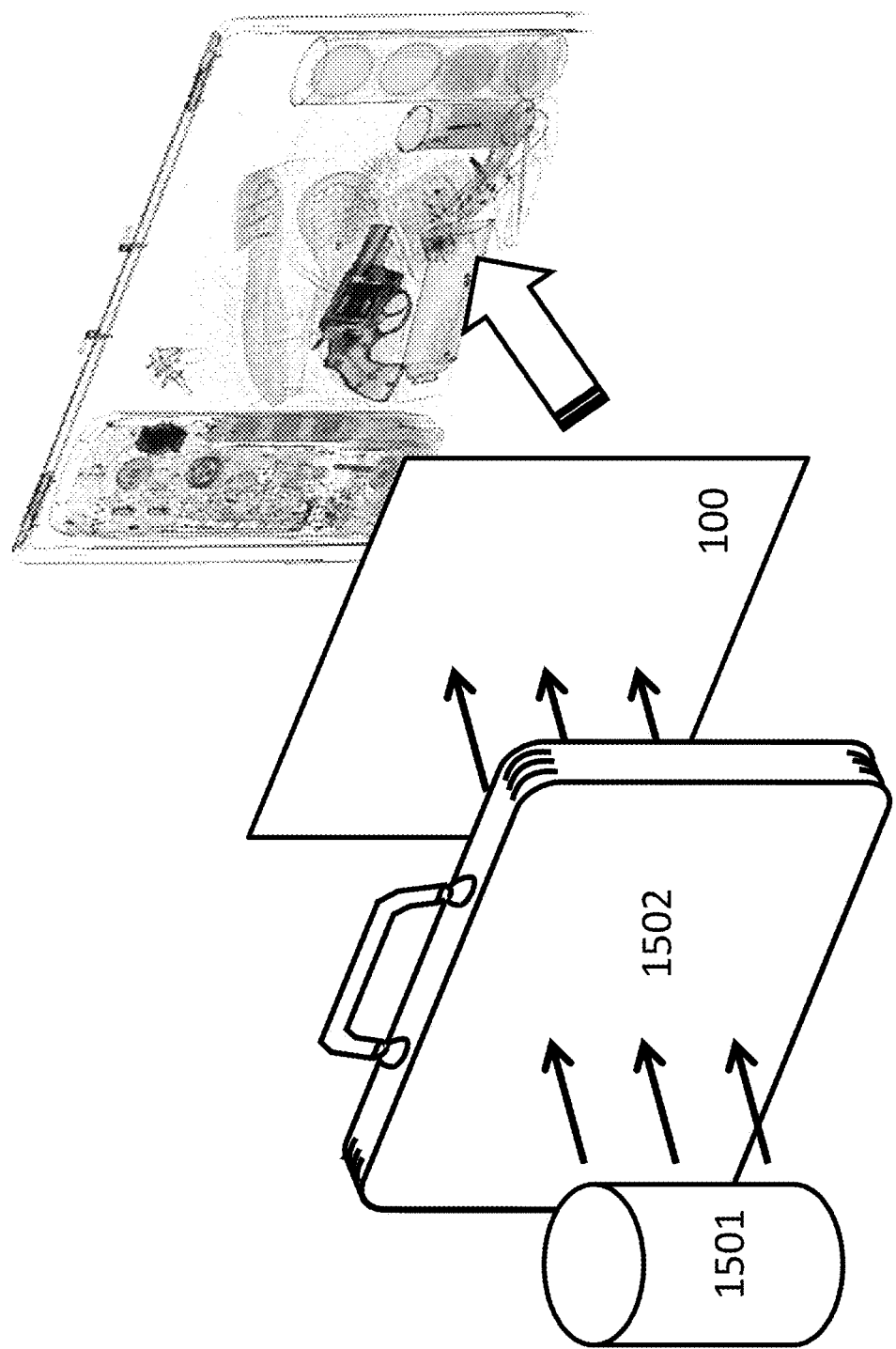
Figure 16:
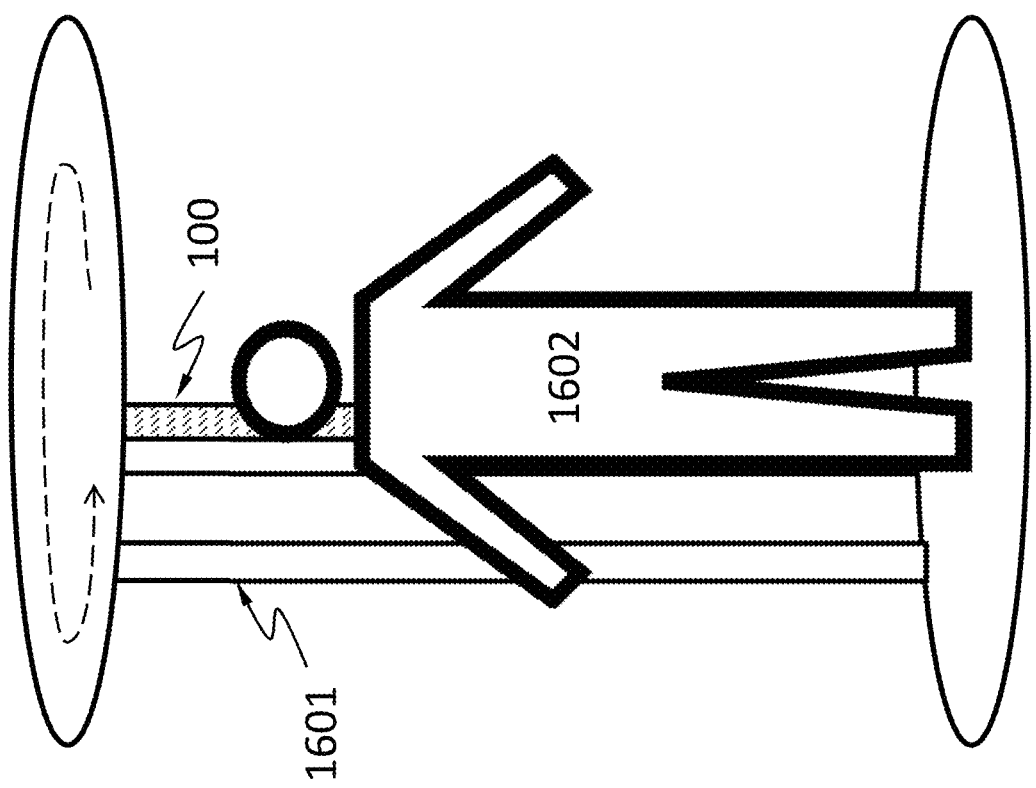
Figure 17:
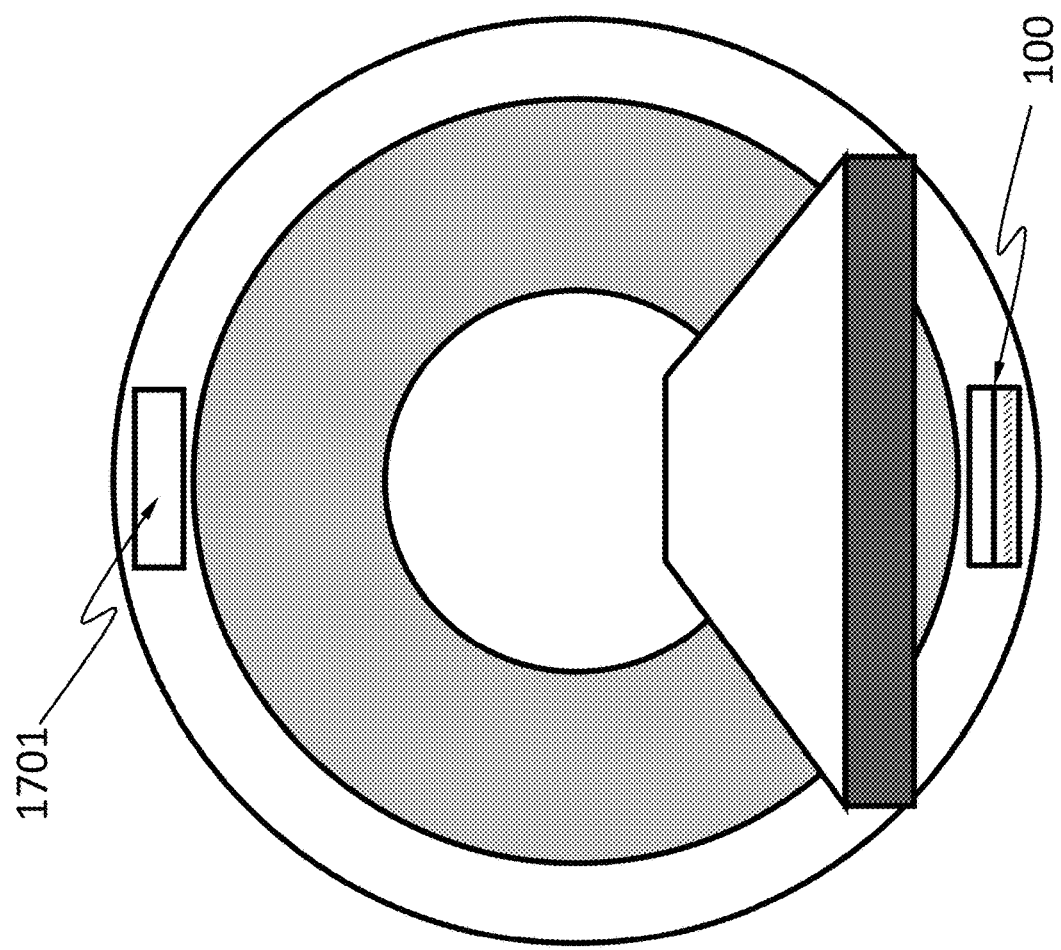
Figure 18:
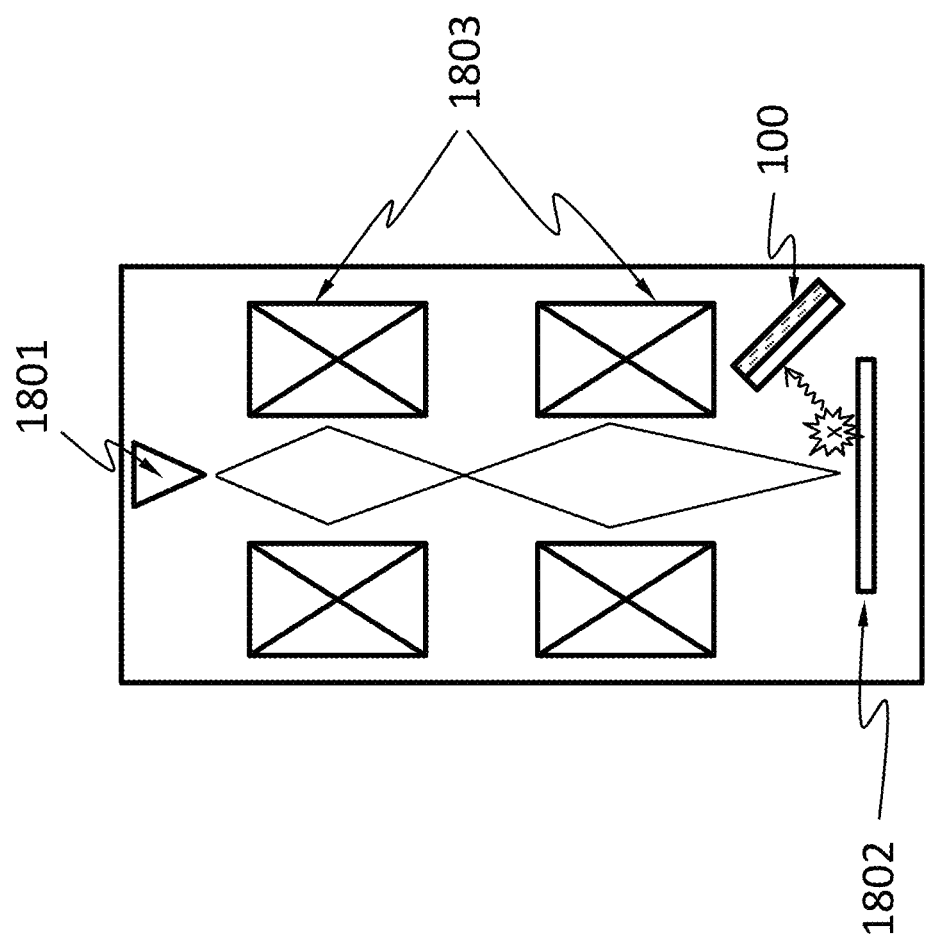
Figure 19:
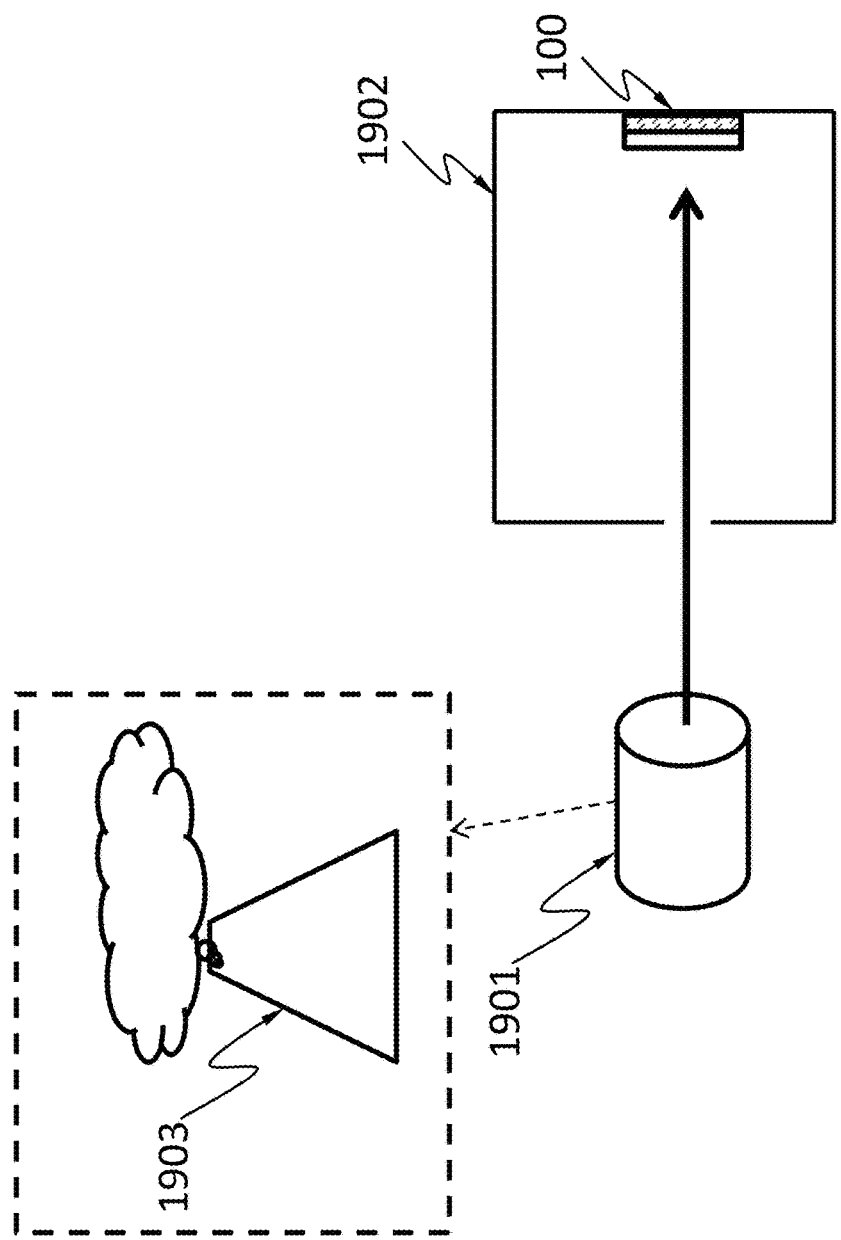

caused by noise (e.g., dark current), and a corresponding temporal change of the voltage of the electrode (lower curve), in the electronic system operating in the way shown in FIG. 4, according to an embodiment;

FIG. 6 shows a flow chart for a method suitable for detecting X-ray based on a system such as the electronic system in FIG. 3A and FIG. 3B, according to an embodiment;

FIG. 7 shows a flow chart for a method suitable for determining whether charge sharing occurs at step 605 in FIG. 6 based on a system such as the electronic system in FIG. 3A and FIG. 3B, according to an embodiment;

FIG. 8A shows an example of a circuit that can implement the method of FIG. 7;

FIGS. 8B-8C schematically show examples of various waveforms with respect to FIG. 8A;

FIG. 9A shows an example of a circuit in addition to the circuit in FIG. 8A that can collectively implement the method of FIG. 7;

FIGS. 9B-9C schematically show examples of various waveforms with respect to FIG. 9A;

FIG. 10 schematically shows a system suitable for phase-contrast X-ray imaging (PCI), according to an embodiment;

FIG. 11 schematically shows a system suitable for phase-contrast X-ray imaging (PCI), according to an embodiment;

FIG. 12 schematically shows a system comprising the semiconductor X-ray detector described herein, suitable for medical imaging such as chest X-ray radiography, abdominal X-ray radiography, etc., according to an embodiment;

FIG. 13 schematically shows a system comprising the semiconductor X-ray detector described herein suitable for dental X-ray radiography, according to an embodiment;

FIG. 14 schematically shows a cargo scanning or non-intrusive inspection (NII) system comprising the semiconductor X-ray detector described herein, according to an embodiment;

FIG. 15 schematically shows another cargo scanning or non-intrusive inspection (NII) system comprising the semiconductor X-ray detector described herein, according to an embodiment;

FIG. 16 schematically shows a full-body scanner system comprising the semiconductor X-ray detector described herein, according to an embodiment;

FIG. 17 schematically shows an X-ray computed tomography (X-ray CT) system comprising a semiconductor X-ray detector described herein, according to an embodiment;

FIG. 18 schematically shows an electron microscope comprising the semiconductor X-ray detector described herein, according to an embodiment; and FIG. 19 schematically shows a radiation dose meter, according to an embodiment.

Figure 20:
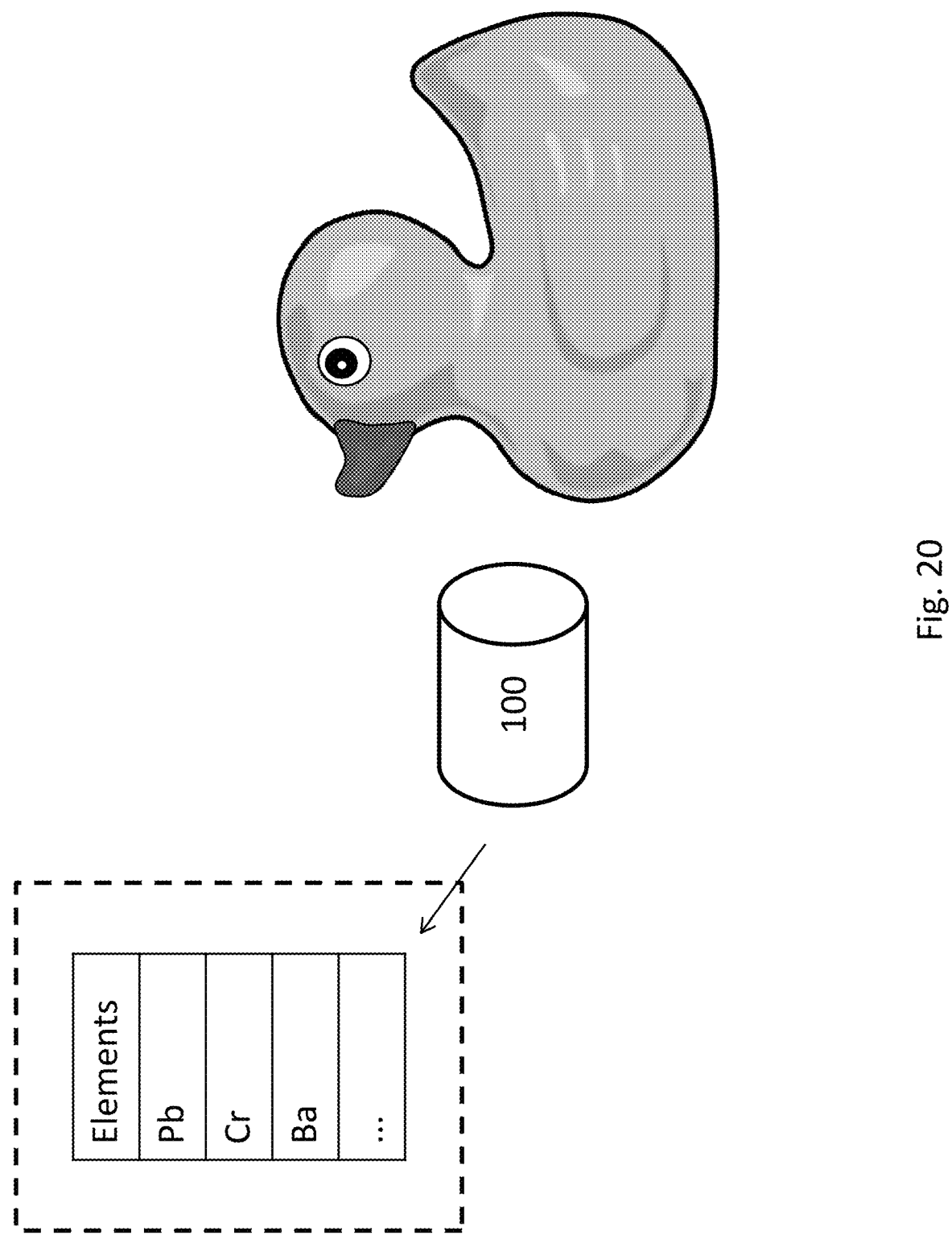

FIG. 20 schematically shows an element analyzer, according to an embodiment.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

When an X-ray photon is absorbed in a semiconductor layer of an X-ray detector having an array of pixels, multiple charge carriers (e.g., electrons and holes) are generated and may be swept under an electric field towards circuitry for measuring these charge carriers. The carriers drift along the direction of the electric field and diffuse in all directions. The envelope of carrier trajectories can be roughly a conical shape. If the envelope sits on a boundary of two or more pixels of the X-ray detector, charge sharing occurs ("charge sharing" used in the present teachings means charge carriers generated from a single X-ray photon are collected by two or more pixels). Charge sharing may cause inaccurate measurement of an X-ray photon energy, because the energy of the X-ray photon is determined by the amount of electric charges it generates.

In the present teaching, when it is determined that neighboring pixels share charges generated by a single photon, voltages detected at the pixels are reset, for example, to zero. This is done so that the energy of the single X-ray photon would not be determined. As a result, the energy of the single X-ray photon is determined only when it is determined that the neighboring pixels do not share the charges generated by the single photon, i.e., the charge sharing does not occur. Various example circuits that may be used to determine whether the charge sharing occurs will be described in great details below.

Figure 1A:
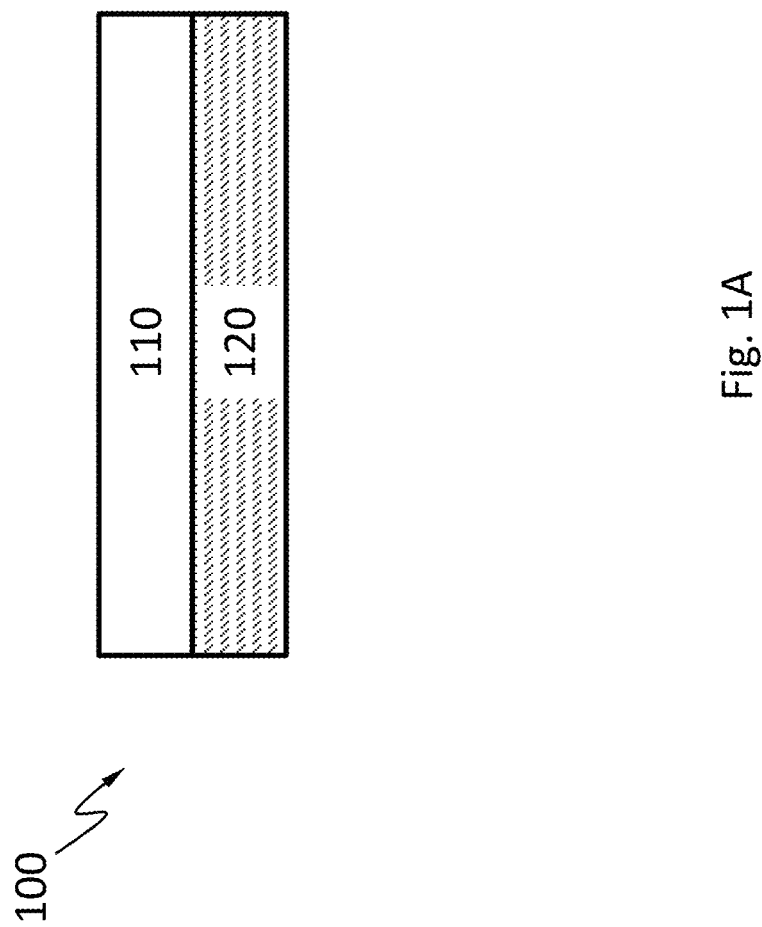
FIG. 1A schematically shows a cross-sectional view of the detector, according to an embodiment.

FIG. 1A schematically shows a semiconductor X-ray detector 100, according to an embodiment. The semiconductor X-ray detector 100 may include an X-ray absorption layer 110 and an electronics layer 120 (e.g., an ASIC) for processing or analyzing electrical signals that X-ray generates in the X-ray absorption layer 110. In an embodiment, the semiconductor X-ray detector 100 does not comprise a scintillator. The X-ray absorption layer 110 may include a semiconductor material such as, silicon, germanium, GaAs, CdTe, CdZnTe, or a combination thereof. The semiconductor may have a high mass attenuation coefficient for the X-ray energy of interest.

Figure 1B:
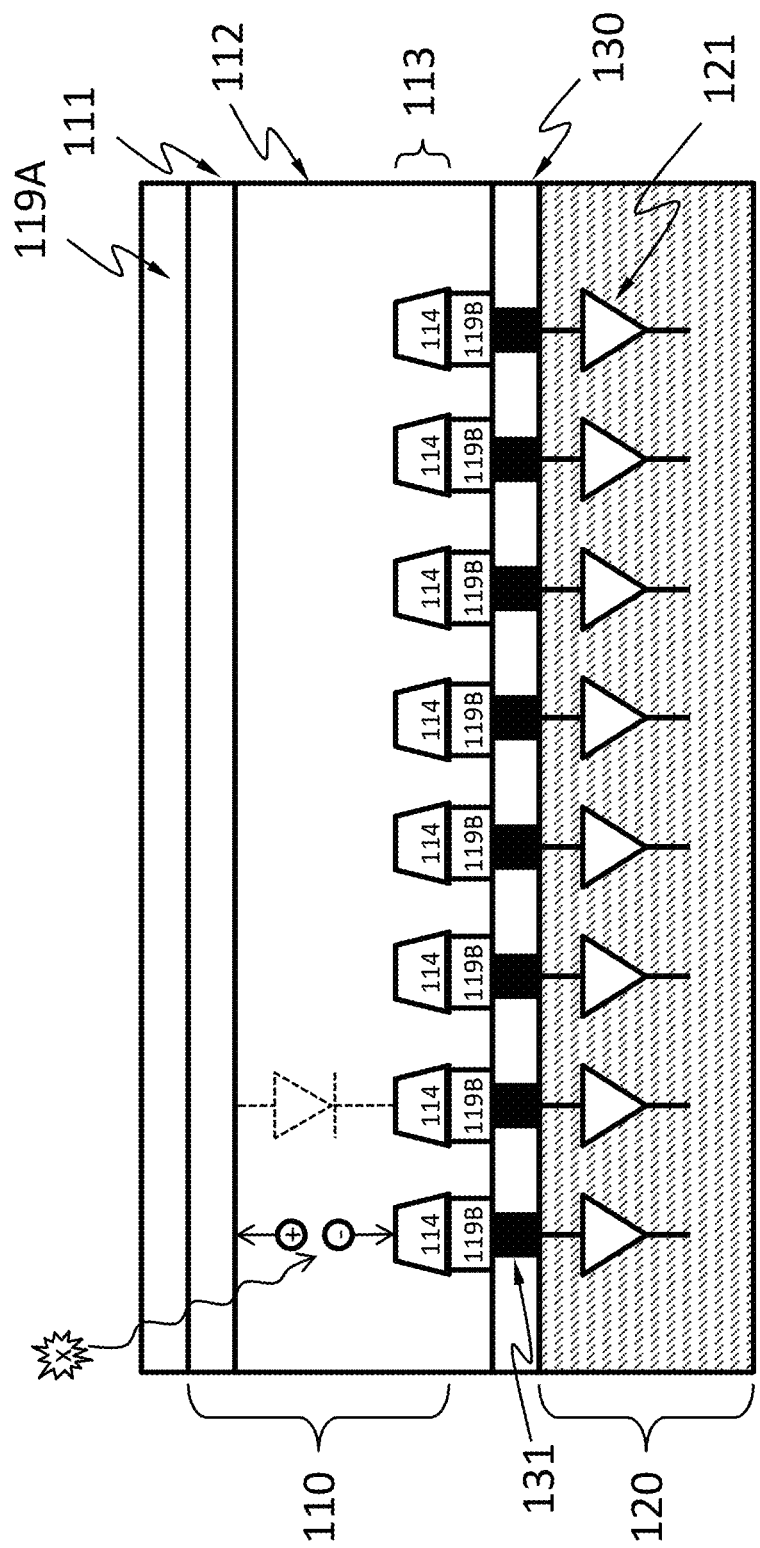
FIG. 1B schematically shows a detailed cross-sectional view of the detector, according to an embodiment.

As shown in a detailed cross-sectional view of the detector 100 in FIG. 1B, according to an embodiment, the X-ray absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete portions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 1B, each of the discrete regions 114 of the second doped region 113 forms a diode with the first doped region 111 and the optional intrinsic region 112. Namely, in the example in FIG. 1B, the X-ray absorption layer 110 has a plurality of diodes having the first doped region 111 as a shared electrode. The first doped region 111 may also have discrete portions.

When an X-ray photon hits the X-ray absorption layer 110 including diodes, the X-ray photon may be absorbed and generate one or more charge carriers by a number of mechanisms. An X-ray photon may generate 10 to 100000 charge carriers. The charge carriers may drift to the electrodes of one of the diodes under an electric field. The field may be an external electric field. The electrical contact 119B may include discrete portions each of which is in electrical contact with the discrete regions 114. In an embodiment, the charge carriers generated by a single X-ray photon can be shared by two different discrete regions 114.

Figure 1C:
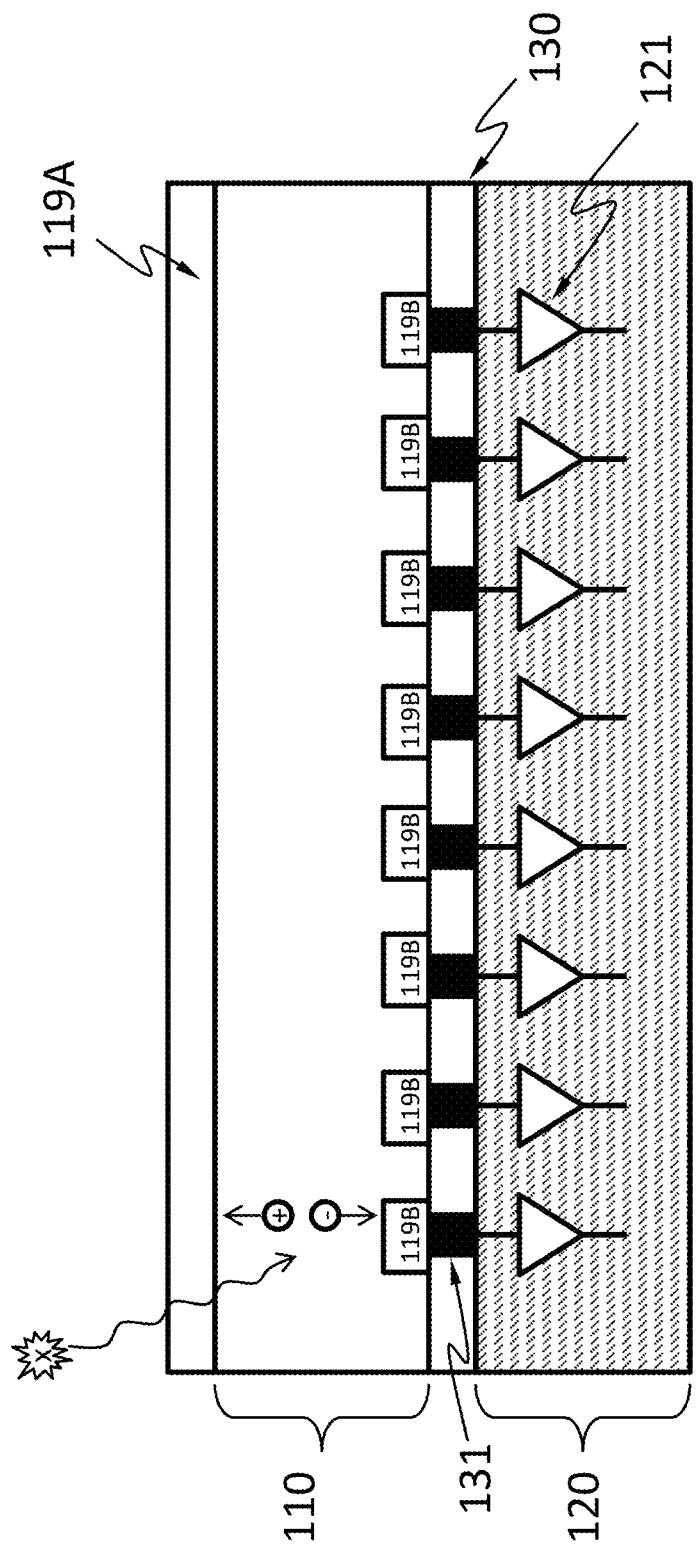
FIG. 1C schematically shows an alternative detailed cross-sectional view of the detector, according to an embodiment.

As shown in an alternative detailed cross-sectional view of the detector 100 in FIG. 1C, according to an embodiment, the X-ray absorption layer 110 may include a resistor of a semiconductor material such as silicon, germanium, GaAs, CdTe, CdZnTe, or a combination thereof, but does not include a diode. The semiconductor may have a high mass attenuation coefficient for the X-ray energy of interest.

When an X-ray photon hits the X-ray absorption layer 110 including a resistor but not diodes, it may be absorbed and generate one or more charge carriers by a number of mechanisms. An X-ray photon may generate 10 to 100000 charge carriers. The charge carriers may drift to the electrical contacts 119A and 119B under an electric field. The field may be an external electric field. The electrical contact 119B includes discrete portions. In an embodiment, the charge carriers generated by a single X-ray photon can be shared by two or more different contacts 119B.

The electronics layer 120 may include an electronic system 121 suitable for processing or interpreting signals generated by X-ray photons incident on the X-ray absorption layer 110. The electronic system 121 may include an analog circuitry such as a filter network, amplifiers, integrators, and comparators, or a digital circuitry such as a microprocessors, and memory. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the X-ray absorption layer 110. Other bonding techniques are possible to connect the electronic system 121 to the pixels without using vias.

Figure 2A:
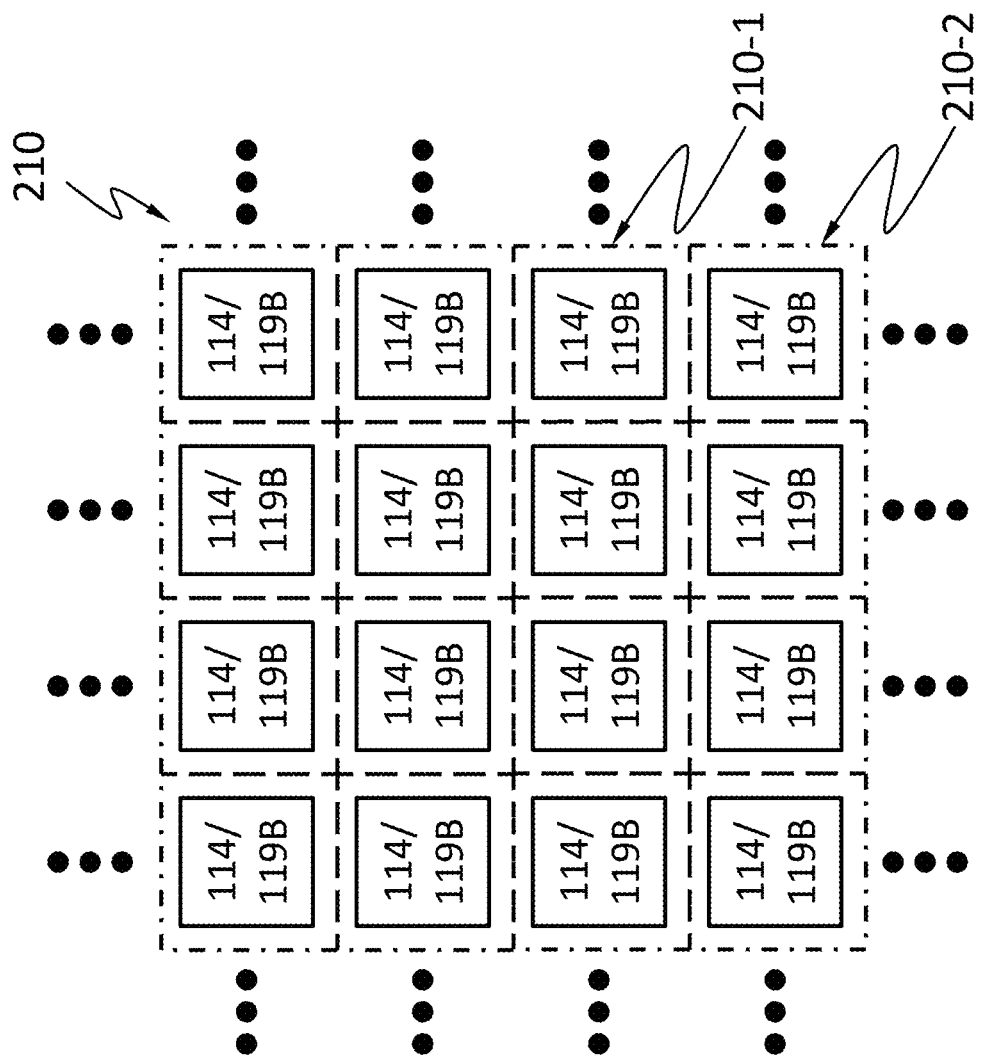
FIG. 2A shows an exemplary top view of a portion of a semiconductor X-ray detector, according to an embodiment.

FIG. 2A shows an exemplary top view of a portion of the device 100 with a 4-by-4 array of discrete regions 114. Charge carriers generated by an X-ray photon incident around the footprint of one of these discrete regions 114 are not substantially shared with another of these discrete regions 114. The area 210 around a discrete region 114 in which substantially all (more than 95%, more than 98% or more than 99% of) charge carriers generated by an X-ray photon incident therein flow to the discrete region 114 is called a pixel associated with that discrete region 114. Namely, less than 5%, less than 2% or less than 1% of these charge carriers flow beyond the pixel, when the X-ray photon hits inside the pixel. The pixels may be organized in any suitable array, such as, a square array, a triangular array and a honeycomb array. The pixels may have any suitable shape, such as, circular, triangular, square, rectangular, and hexagonal. The pixels may be individually addressable.

Similarly, when the 4-by-4 array in FIG. 2A indicates an array of discrete portions of the electrical contact 119B in FIG. 1B, the charge carriers generated by an X-ray photon incident around the footprint of one of these discrete portions of the electrical contact 119B are not substantially shared with another of these discrete portions of the electrical contact 119B. The area around a discrete portion of the electrical contact 119B in which substantially all (more than 95%, more than 98% or more than 99% of) charge carriers generated by an X-ray photon incident therein flow to the discrete portion of the electrical contact 119B is called a pixel associated with the discrete portion of the electrical contact 119B. Namely, less than 5%, less than 2% or less than 1% of these charge carriers flow beyond the pixel associated with the one discrete portion of the electrical contact 119B, when the X-ray photon hits inside the pixel. The pixels may be organized in any suitable array, such as, a square array, a triangular array and a honeycomb array. The pixels may have any suitable shape, such as, circular, triangular, square, rectangular, and hexagonal. The pixels may be individually addressable.

As shown in FIG. 2A, two pixels 210 (e.g. 210-1 and 210-2) associated with two neighboring discrete regions 114 can be called two neighboring pixels ("neighboring pixels" used in the present teaching means pixels that are close to each other such that carriers generated from a single photon may be shared by these pixels).

Figure 2B:
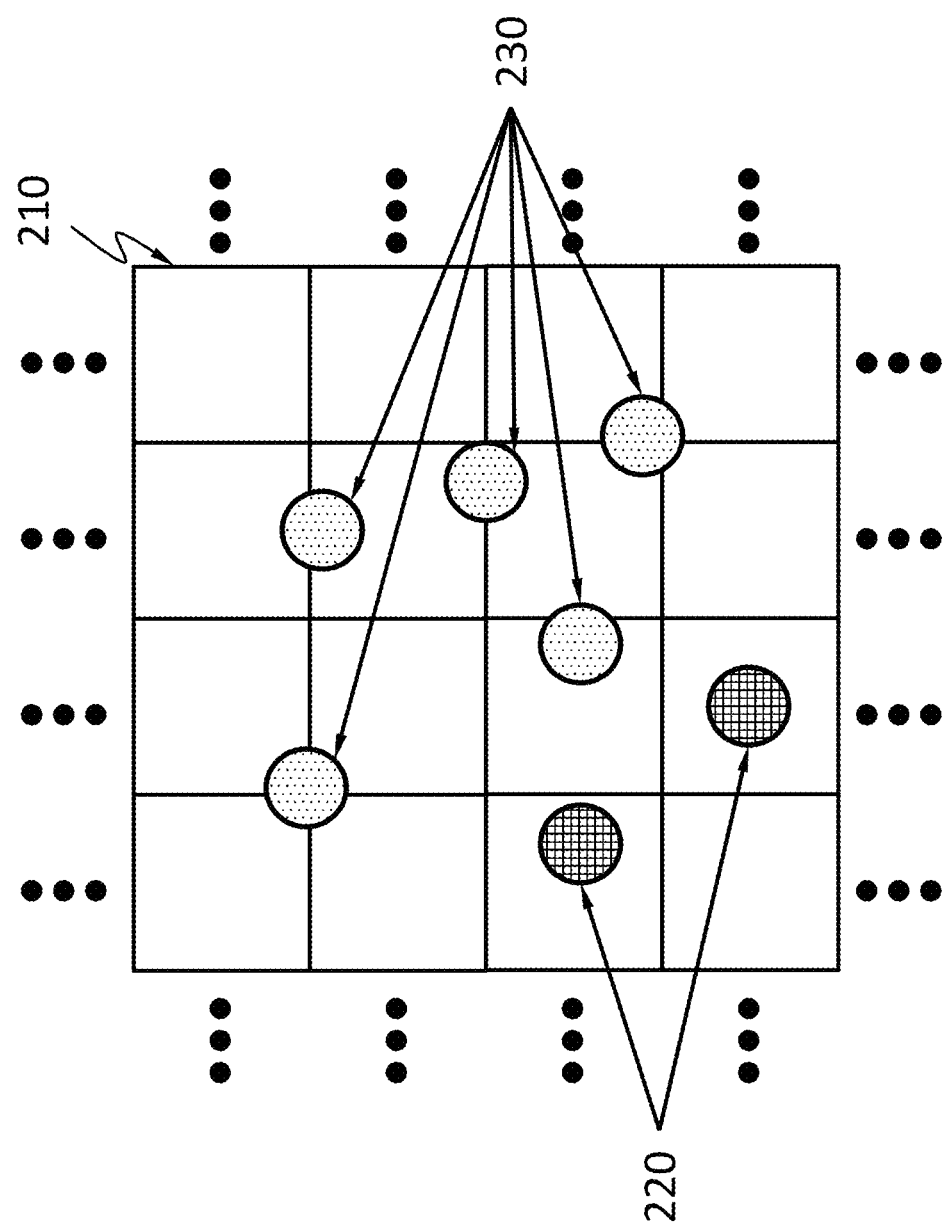
FIG. 2B shows an exemplary array of pixels in a semiconductor X-ray detector, according to an embodiment.

FIG. 2B shows an exemplary array of pixels in a semiconductor X-ray detector, according to an embodiment. When an X-ray photon hits the array, it may be absorbed and cause multiple charge carriers to be generated. The carriers may transport in various directions, e.g. drift along the direction of an electric field and diffuse in all directions. In FIG. 2B, each circle (e.g. 220, 230) represents the footprint of a transport area of charge carriers generated by a photon ("transport area" used in the present teaching means a space the carriers generated by a photon are transported into).

As shown in FIG. 2B, a transport area may sit inside a pixel (e.g. transport areas 220), or on a boundary of neighboring pixels (e.g. transport areas 230).

As discussed above, when a transport area sits on a boundary of two or more neighboring pixels, charge sharing occurs, which may cause issues for energy measurement. Charge sharing may also lead to errors in counting the number photons.

According to an embodiment, two neighboring pixels do not have to share a boundary, but can be close to each other such that carriers generated from a single photon may be shared by the two pixels. That is, charge sharing may occur on neighboring pixels, even if there is not a boundary shared by the neighboring pixels.

A size of a pixel can be determined by design, based on fabrication process. As shown in FIG. 2B, the size of each pixel is designed to be the same and enough to cover a transport area when the corresponding photon hits around the center of the pixel. If the size of a pixel is too small, e.g. smaller than a transport area, then charge sharing can happen all the time. On the other hand, if the size of a pixel is too large, it is very likely for multiple photons to hit the pixel at the same time, which can generate difficulty for accurate X-ray detection and image generation.

FIG. 3A and FIG. 3B each show a component diagram of the electronic system 121, according to an embodiment. The electronic system 121 may include a first voltage comparator 301, a second voltage comparator 302, a counter 320, a switch 305, a voltmeter 306 and a controller 310.

The first voltage comparator 301 is configured to compare the voltage of an electrode of a diode 300 to a first threshold. The diode may be a diode formed by the first doped region 111, one of the discrete regions 114 of the second doped region 113, and the optional intrinsic region 112. Alternatively, the first voltage comparator 301 is configured to compare the voltage of an electrical contact (e.g., a discrete portion of electrical contact 119B) to a first threshold. The first voltage comparator 301 may be configured to monitor the voltage directly, or calculate the voltage by integrating an electric current flowing through the diode or electrical contact over a period of time. The first voltage comparator 301 may be controllably activated or deactivated by the controller 310. The first voltage comparator 301 may be a continuous comparator. Namely, the first voltage comparator 301 may be configured to be activated continuously, and monitor the voltage continuously. The first voltage comparator 301 configured as a continuous comparator reduces the chance that the system 121 misses signals generated by an incident X-ray photon. The first voltage comparator 301 configured as a continuous comparator is especially suitable when the incident X-ray intensity is relatively high. The first voltage comparator 301 may be a clocked comparator, which has the benefit of lower power consumption. The first voltage comparator 301 configured as a clocked comparator may cause the system 121 to miss signals generated by some incident X-ray photons. When the incident X-ray intensity is low, the chance of missing an incident X-ray photon is low because the time interval between two successive photons is relatively long. Therefore, the first voltage comparator 301 configured as a clocked comparator is especially suitable when the incident X-ray intensity is relatively low. The first threshold may be 5-10%, 10%-20%, 20-30%, 30-40% or 40-50% of the maximum voltage one incident X-ray photon may generate in the diode or the resistor. The maximum voltage may depend on the energy of the incident X-ray photon (i.e., the wavelength of the incident X-ray), the material of the X-ray absorption layer 110, and other factors. For example, the first threshold may be 50 mV, 100 mV, 150 mV, or 200 mV.

The second voltage comparator 302 is configured to compare the voltage to a second threshold V2. The second voltage comparator 302 may be configured to monitor the voltage directly, or calculate the voltage by integrating an electric current flowing through the diode or the electrical contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold V2 is greater than the absolute value of the first threshold. As used herein, the term "absolute value" or "modulus" |x| of a real number x is the non-negative value of x without regard to its sign. Namely, $$|x| = \begin{cases} x, \text{ if } x \geq 0 \\ -x, \text{ if } x \leq 0 \end{cases}.$$

The second threshold V2 may be 200%-300% of the first threshold. The second threshold V2 may be at least 50% of the maximum voltage one incident X-ray photon may generate in the diode or resistor. For example, the second threshold V2 may be 100 mV, 150 mV, 200 mV, 250 mV or 300 mV. The second voltage comparator 302 and the first voltage comparator 310 may be the same component. Namely, the system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the system 121 to operate under a high flux of incident X-ray. However, having a high speed is often at the cost of power consumption.

The counter 320 is configured to register a number of X-ray photons reaching the diode or resistor. The counter 320 may be a software component (e.g., a number stored in a computer memory) or a hardware component (e.g., a 4017 IC and a 7490 IC).

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause the number registered by the counter 320 to increase by one, if, during the time delay, the second voltage comparator 302 determines that the absolute value of the voltage equals or exceeds the absolute value of the second threshold V2.

The controller 310 may be configured to cause the voltmeter 306 to measure the voltage upon expiration of the time delay. The controller 310 may be configured to connect the electrode to an electrical ground, so as to reset the voltage and discharge any charge carriers accumulated on the electrode. In an embodiment, the electrode is connected to an electrical ground after the expiration of the time delay. In an embodiment, the electrode is connected to an electrical ground for a finite reset time period. The controller 310 may connect the electrode to the electrical ground by controlling the switch 305. The switch may be a transistor such as a field-effect transistor (FET).

In an embodiment, the system 121 has no analog filter network (e.g., a RC network). In an embodiment, the system 121 has no analog circuitry.

The voltmeter 306 may feed the voltage it measures to the controller 310 as an analog or digital signal.

The system 121 may include a capacitor module 309 electrically connected to the electrode of the diode 300 or the electrical contact, wherein the capacitor module is configured to collect charge carriers from the electrode. The capacitor module can include a capacitor in the feedback path of an amplifier. The amplifier configured as such is called a capacitive trans-impedance amplifier (CTIA). CTIA has high dynamic range by keeping the amplifier from saturating and improves the signal-to-noise ratio by limiting the bandwidth in the signal path. Charge carriers from the electrode accumulate on the capacitor over a period of time ("integration period") (e.g., as shown in FIG. 4, between $t_0$ to $t_1$, or $t_1$-t2). After the integration period has expired, the capacitor voltage is sampled and then reset by a reset switch. The capacitor module can include a capacitor directly connected to the electrode.

FIG. 4 schematically shows a temporal change of the electric current flowing through the electrode (upper curve) caused by charge carriers generated by an X-ray photon incident on the diode or the resistor, and a corresponding temporal change of the voltage of the electrode (lower curve). The voltage may be an integral of the electric current with respect to time. At time to, the X-ray photon hits the diode or the resistor, charge carriers start being generated in the diode or the resistor, electric current starts to flow through the electrode of the diode or the resistor, and the absolute value of the voltage of the electrode or electrical contact starts to increase. At time t1, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold V2 at time $t_2$, the controller 310 causes the number registered by the counter 320 to increase by one. At time $t_e$, all charge carriers generated by the X-ray photon drift out of the X-ray absorption layer 110. At time $t_s$, the time delay TD1 expires. In the example of FIG. 4, time $t_s$ is after time $t_e$; namely TD1 expires after all charge carriers generated by the X-ray photon drift out of the X-ray absorption layer 110. The rate of change of the voltage is thus substantially zero at $t_s$. The controller 310 may be configured to deactivate the second voltage comparator 302 at expiration of TD1 or at $t_2$, or any time in between.

The controller 310 may be configured to cause the voltmeter 306 to measure the voltage upon expiration of the time delay TD1. In an embodiment, the controller 310 causes the voltmeter 306 to measure the voltage after the rate of change of the voltage becomes substantially zero after the expiration of the time delay TD1. The voltage at this moment is proportional to the amount of charge carriers generated by an X-ray photon, which relates to the energy of the X-ray photon. The controller 310 may be configured to determine the energy of the X-ray photon based on voltage the voltmeter 306 measures. One way to determine the energy is by binning the voltage. The counter 320 may have a sub-counter for each bin. When the controller 310 determines that the energy of the X-ray photon falls in a bin, the controller 310 may cause the number registered in the sub-counter for that bin to increase by one. Therefore, the system 121 may be able to detect an X-ray image and may be able to resolve X-ray photon energies of each X-ray photon.

After TD1 expires, the controller 310 connects the electrode to an electric ground for a reset period RST to allow charge carriers accumulated on the electrode to flow to the ground and reset the voltage. After RST, the system 121 is ready to detect another incident X-ray photon. Implicitly, the rate of incident X-ray photons the system 121 can handle in the example of FIG. 4 is limited by 1/(TD1+RST). If the first voltage comparator 301 has been deactivated, the controller 310 can activate it at any time before RST expires. If the controller 310 has been deactivated, it may be activated before RST expires.

Figure 5:
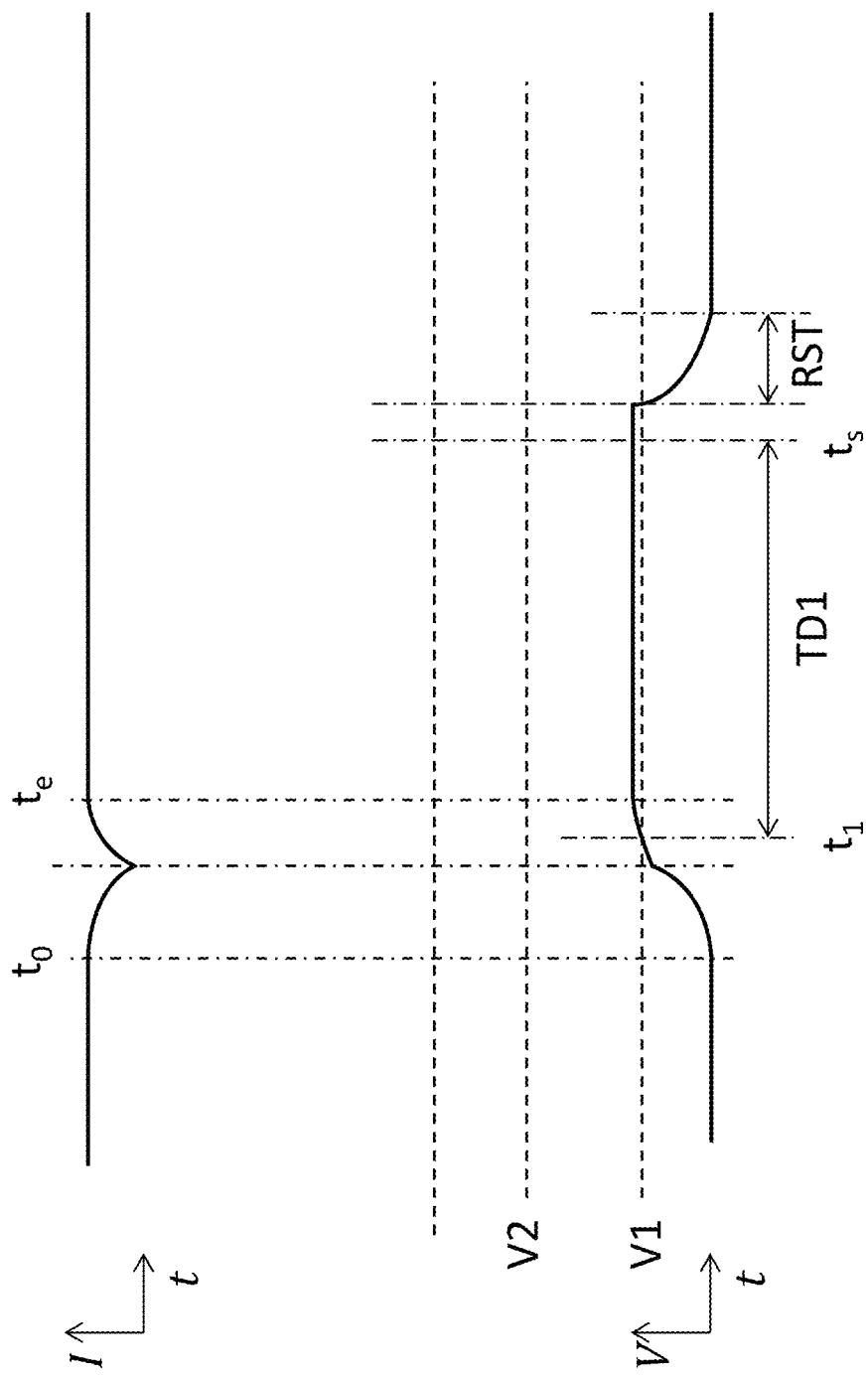
FIG. 5 schematically shows a temporal change of the electric current flowing through the electrode (upper curve)

FIG. 5 schematically shows a temporal change of the electric current flowing through the electrode (upper curve) caused by noise (e.g., dark current, background radiation, scattered X-rays, fluorescent X-rays, shared charges from adjacent pixels), and a corresponding temporal change of the voltage of the electrode (lower curve), in the system 121 operating in the way shown in FIG. 4. At time to, the noise begins. If the noise is not large enough to cause the absolute value of the voltage to exceed the absolute value of V1, the controller 310 does not activate the second voltage comparator 302. If the noise is large enough to cause the absolute value of the voltage to exceed the absolute value of V1 at time t1 as determined by the first voltage comparator 301, the controller 310 starts the time delay TD1 and the controller 310 may deactivate the first voltage comparator 301 at the beginning of TD1. During TD1 (e.g., at expiration of TD1), the controller 310 activates the second voltage comparator 302. The noise is very unlikely large enough to cause the absolute value of the voltage to exceed the absolute value of V2 during TD1. Therefore, the controller 310 does not cause the number registered by the counter 320 to increase. At time $t_e$, the noise ends. At time $t_s$, the time delay TD1 expires. The controller 310 may be configured to deactivate the second voltage comparator 302 at expiration of TD1. The controller 310 may be configured not to cause the voltmeter 306 to measure the voltage if the absolute value of the voltage does not exceed the absolute value of V2 during TD1. After TD1 expires, the controller 310 connects the electrode to an electric ground for a reset period RST to allow charge carriers accumulated on the electrode as a result of the noise to flow to the ground and reset the voltage. Therefore, the system 121 may be very effective in noise rejection.

FIG. 6 shows a flow chart for a method suitable for detecting X-ray based on a system such as the electronic system in FIG. 3A and FIG. 3B, according to an embodiment. At 902, a voltage of an electrode is determined. The electrode may be a diode or an electrical contact of a resistor in a pixel exposed to X-ray. At 605, it is determined whether a neighboring pixel shares the charges generated by a single X-ray photon, i.e., whether charge sharing occurs. If so, the process proceeds to 604. Otherwise, the process proceeds to 606. More details about 605 will be discussed in FIG. 7. At 604, the voltage is reset when the charge sharing occurs. In an embodiment, the value of the voltage is reset to zero, i.e., the voltage is reset to an electrical ground, e.g., by connecting the electrode of the diode or an electrical contact of a resistor to an electrical ground. In an embodiment, the voltage is erased. As a result, the energy of the single X-ray photon will not be determined. Then, the process returns to 602 for detecting another X-ray.

At 606, an absolute value of the voltage of an electrode of a diode or an electrical contact of a resistor exposed to X-ray, is compared, e.g., by the first voltage comparator 301, to a first threshold V1. At 607, if the absolute value of the voltage does not equal or exceed the absolute value of the first threshold, the process goes back to 606. If the absolute value of the voltage equals or exceeds the absolute value of the first threshold at 607, the process continues to 608, e.g. after a time delay or after the voltage is stabilized. At 608, the absolute value of the voltage is compared, e.g., using the second voltage comparator 302, to a second threshold V2. Then, the process moves to 615.

At 615, if the absolute value of the voltage does not equal or exceed the absolute value of the second threshold V2, the process goes to 620. If the absolute value of the voltage equals or exceeds the absolute value of the second threshold V2, the process continues to step 616. At 616, the number registered in the counter 320 is caused, e.g., by the controller 320, to increase by one. At 618, the X-ray photon energy is determined, e.g., by the controller 336, based on the voltage. In an embodiment, there may be a counter for each of the energy bins. After measuring the X-ray photon energy, the counter for the bin to which the photon energy belongs can be increased by one. The process goes to 620 after 618. At 620, the voltage is reset to an electrical ground, e.g., by connecting the electrode of the diode or an electrical contact of a resistor to an electrical ground. After 620, the process may go back to 602.

FIG. 7 shows a flow chart for a method suitable for determining whether charge sharing occurs as step 605 in FIG. 6 based on a system such as the electronic system in FIG. 3A and FIG. 3B, according to an embodiment. The process starts at 710 after 602 as described above. At 710, a first waveform of voltage is obtained. The first waveform of voltage illustrates a temporal profile of the voltage of a diode or an electrical contact of a resistor at one of the pixels. At 720, a neighboring pixel of the one of the pixels is found. At 730, a second waveform of voltage detected at the neighboring pixel is obtained. The second waveform of voltage illustrates a temporal profile of the voltage of a diode or an electrical contact of a resistor at the neighboring pixel. At 740, a characteristic associated with the first and the second waveforms of voltages is determined. In an embodiment, the characteristic associated with the first and the second waveforms of voltages is a time difference between a rising or falling edge of the first voltage and the rising or falling edge of the second voltage. The characteristic may be determined directly as an output of a circuit. Alternatively, the characteristic may be determined indirectly, e.g., based on two or more outputs of circuits. For example, a first time corresponding to the rising or falling edge of the first voltage, and a second time corresponding to the rising or falling edge of the second voltage are determined respectively. Then the characteristic (i.e., the time difference) may be determined by comparing the first time and the second time. At 750, if the characteristic is within a threshold, the process moves to 760. Otherwise, the process moves to 770.

In an embodiment, at 740, the characteristic associated with the first and the second waveforms of voltages is a function of the time difference between the rising or falling edge of the first voltage and the rising or falling edge of the second voltage. To generate such characteristic, the time difference obtained above may be used as an input to an additional circuit. At 750, if the characteristic is greater than a threshold, the process moves to 760. Otherwise, the process moves to 770.

At 760, it is determined that charge sharing occurs. Then, the process moves to 604 as described above. At 770, if there is one more neighboring pixel, the process moves to 720. Otherwise, the process moves to 780. At 780, it is determined that charge sharing does not occur. Then, the process proceeds to 606 as described above. Although the flowchart in FIG. 7 shows that charge sharing with neighboring pixels is determined serially, charge sharing with neighboring pixels may be determined in parallel.

FIG. 8A shows an example of a circuit that can implement the method of FIG. 7. The circuit is to output a signal, t_charge, which characterizes the time difference between the rising edge of the first waveform of voltage, S1, and the rising edge of the second waveform of voltage, S2. In this example, the circuit includes a first D-type flip-flop (DFF) 810, a NAND gate 830, a delay element 820, a first NOT gate 812, a second NOT gate 814, a second DFF 815, and an exclusive-OR (XOR) gate 840.

As shown, both the first DFF 810 and the second DFF 815 are connected to a power source VDD. The first waveform of voltage, S1, e.g., determined at a pixel, is inputted to the first DFF 810. The second waveform of voltage, S2, e.g., determined at a neighboring pixel, is inputted to the second DFF 815. As shown in FIG. 8A, the outputs of the first DFF 810 and the second DFF 815 are represented as "Up" and "Down," respectively.

Further, the outputs of the first DFF 810 and the second DFF 815 are inputted to the NAND gate 830. The NAND gate 830 is configured to output a low voltage, i.e., "0" when both the first DFF 810 and the second DFF 815 output a high voltage, i.e., "1." The NAND gate 830 is further configured to output a high voltage, i.e., "1" when either the first DFF 810 or the second DFF 815 outputs a low voltage, i.e., "0."

The delay element 820 temporally delays the output of the NAND gate 830. The output of the delay element 820 is inputted to the first DFF 810 and the second DFF 815 through the first NOT gate 812 and the second NOT gate 814, respectively. The first NOT gate 812 and the second NOT gate 814 may be configured to invert the output of the delay element 820 as the input to the first DFF 810 and the second DFF 815, respectively. For example, when the output of the delay element 820 is a low voltage, i.e., "0," after inverted by the first NOT gate 812 and/or the second NOT gate 814, the high voltage, i.e., "1," is inputted to the first DFF 810 and/or the second DFF 815. Alternatively, when the output of the delay element 820 is a high voltage, i.e., "1," after inverted by the first NOT gate 812 and/or the second NOT gate 814, the low voltage, i.e., "0," is inputted to the first DFF 810 and/or the second DFF 815.

The XOR gate 840 receives the outputs of the first DFF 810 and the second DFF 815, i.e., "Up" and "Down" as shown in FIG. 8A as inputs and finally outputs the signal, t_charge. The XOR gate 840 is configured to output a high voltage, i.e., "1" when one of the first DFF 810 and the second DFF 815 outputs a low voltage, i.e., "0," and the other outputs a high voltage, i.e., "1." The XOR gate 840 is further configured to output a low voltage, i.e., "0" when both of the first DFF 810 and the second DFF 815 output a low voltage, i.e., "0," or a high voltage, i.e., "1."

FIG. 8B schematically shows an example of various waveforms of voltages with respect to FIG. 8A, such as "S1," "S2," "Up," "Down," and "t_charge." In this example, the rising edge 850 of the first waveform of voltage, S1, occurs earlier than the rising edge 860 of the second waveform of voltage, S2. As shown in the bottom of FIG. 8B, the resulting output of the circuit, i.e., t_charge, includes a square waveform, the width of which may be represented as "Δt₁" indicating the time difference between the rising edge 850 of the first waveform of voltage, S1, and the rising edge 860 of the second waveform of voltage, S2. As described above, the time difference, Δt₁ may be further compared with a threshold, which may be, e.g., 10 μs, 1 μs, 100 ns, 10 ns, etc. When the time difference Δt₁ is within the threshold, it is determined that charge sharing occurs. Otherwise, it is determined that charge sharing does not occur.

FIG. 8C schematically shows another example of various waveforms of voltages with respect to FIG. 8A, such as "S1," "S2," "Up," "Down," and "t_charge." In this example, the rising edge 870 of the first waveform of voltage, S1, occurs later than the rising edge 880 of the second waveform of voltage, S2. As shown in the bottom of FIG. 8C, the resulting output of the circuit, i.e., t_charge, includes a square waveform, the width of which may be represented as "Δ₂" indicating the time difference between the rising edge 870 of the first waveform of voltage, S1, and the rising edge 880 of the second waveform of voltage, S2. As described above, the time difference, Δt₂ may be further compared with a threshold, which may be, e.g., 10 μs, 1 μs, 100 ns, 10 ns, etc. When the time difference Δt₂ is within the threshold, it is determined that charge sharing occurs. Otherwise, it is determined that charge sharing does not occur.

FIG. 9A shows an example of a circuit in addition to the circuit in FIG. 8A that can collectively implement the method of FIG. 7. The circuit is to output a signal, v_charge, which is a function of the time difference between the rising edge of the first waveform of voltage, S1, and the rising edge of the second waveform of voltage, S2. The circuit is to further output a decision signal, out, indicating whether charge sharing occurs or not based on comparison between the signal, v_charge and a predetermined reference voltage, v_ref.

In this example, the circuit includes an inverter 910, a current source 920, a P-channel field effect transistor (P-FET) 930, an N-channel field effect transistor (N-FET) 940, a capacitor 950, and a comparator 960.

The inverter 910 is similar to the first NOT gate 812 and the second Not gate 814 as shown in FIG. 8A. The inverter 910 receives and inverts the signal, t_charge. Specifically, when the signal, t_charge is a low voltage, i.e., "0," the inverter 910 outputs a high voltage, i.e., "1." Alternatively or in addition, when the signal, t_charge is a high voltage, i.e., "1," the inverter 910 outputs a low voltage, i.e., "0."

The current source 920 is connected to a power source VDD, and provides a constant electrical current, e.g., represented by I. The P-FET 930 has three ports including a gate ("G"), a source ("S"), and a drain ("D"). When the voltage between the gate and source of the P-FET 930, i.e., $V_{PGS}$ is smaller than a threshold voltage, $V_{PT}$, the P-FET 930 is turned on. Thus, the source may be considered to be shorted with the drain. Otherwise, the P-FET 930 is turned off. Thus, the source may be considered to be disconnected from the drain. To make it simpler, the P-FET 930 may be considered to be turned on when the gate of the P-FET 930 has a low voltage ("0"), and may be considered to be turned off when the gate of the P-FET 930 has a high voltage ("1").

The N-FET 940 has three ports including a gate ("G"), a source ("S"), and a drain ("D"). As shown, the gate of the N-FET 940 is connected to the gate of the P-FET 930, and the output of the inverter 910. The drain of the P-FET 930 is connected to the drain of the N-FET 940, the voltage of which with respect to the ground is represented as v_charge as shown in FIG. 9A. When the voltage between the gate and source of the N-FET 940, i.e., $V_{NGS}$ is greater than a threshold voltage, VNT, the N-FET 940 is turned on. Thus, the source may be considered to be shorted with the drain. Otherwise, the N-FET 940 is turned off. Thus, the source may be considered to be disconnected from the drain. As shown in FIG. 9A, the source of the N-FET 940, in this example, is grounded. To make it simpler, the N-FET 940 may be considered to be turned on when the gate of the N-FET 940 has a high voltage ("1"), and may be considered to be turned off when the gate of the N-FET 940 has a low voltage ("0").

The capacitor 950 may be charged when the P-FET 930 is turned on and the NFET 940 is turned off, thereby producing positive voltage for v_charge. In this example, the positive portion of the voltage, v_charge is proportional to the time. The peak of v_charge is proportional to the width of the corresponding square waveform represented by t_charge, and may be expressed by:

$$V\_charge\_peak = \frac{I\Delta t}{C} \qquad (1)$$

where V_charge_peak represents the peak of the v_charge voltage, I represents the constant current from the current source, Δt represents the width of the square waveform t_charge, and C represents the capacitance of the capacitor 950.

The capacitor 950 may be discharged when the P-FET 930 is turned off and the N-FET 940 is turned on, thereby resulting in zero voltage for v_charge.

The comparator 960 compares v_charge and the predetermined reference voltage, v_ref, and finally generates a decision signal, out, which may include a high voltage ("1") when the corresponding portion of v_charge is greater than the predetermined reference voltage, v_ref and may also include a low voltage ("0") when the corresponding portion of v_charge is smaller than the predetermined reference voltage, v_ref. In an embodiment, the predetermined reference voltage may be any positive voltage. Further, whether charge sharing occurs may be determined based on the decision signal, out. When the decision signal, out, has a low voltage ("0") at all times, it is determined that charge sharing occurs. Otherwise, it is determined that charge sharing does not occur.

In operation, when t_charge has a low voltage ("0"), the output of the inverter 910 has a high voltage ("1"). Thus, the P-FET 930 is turned off and the N-FET 940 is turned on. As a result, the capacitor 950 is discharging as long as t_charge remains in low voltage ("0"). Since the capacitor 950 is grounded, v_charge has a low voltage ("0"). Accordingly, the out signal has a low voltage ("0").

Alternatively, when t_charge has a high voltage ("1"), the output of the inverter 910 has a low voltage ("0"). Thus, the P-FET 930 is turned on and the N-FET 940 is turned off. As a result, the capacitor 950 is charging by the current source 920 as long as t_charge remains in high voltage ("1"). The signal v_charge linearly increases until t_charge transitions from the high voltage ("1") to the low voltage ("0"). The peak of the v_charge is proportional to the width of square waveform represented as t_charge.

In either case, the v_charge voltage is compared with the predetermined threshold voltage, v_ref, thus outputting the decision signal, out. The decision signal, out, has a low voltage ("0") when the v_charge voltage is smaller than the predetermined threshold voltage, v_ref. The decision signal, out, has a high voltage ("1") when the v_charge voltage is greater than the predetermined threshold voltage, v_ref.

Further, whether charge sharing occurs may be determined based on the decision signal, out. When the decision signal, out, has a low voltage ("0") at all times, it is determined that charge sharing occurs. Otherwise, it is determined that charge sharing does not occur.

FIG. 9B schematically shows an example of various waveforms with respect to FIG. 9A. As shown, the v_charge signal starts linearly increasing with respect to time when t_charge transitions from the low voltage ("0") to the high voltage ("1") and returns to zero when t_charge transitions from the high voltage ("1") to the low voltage ("0"). The corresponding decision signal, out, has a high voltage ("1"), when v_charge is greater than the predetermined reference voltage, v_ref, and has a low voltage ("0") otherwise. As described above, it may be determined that, in this case, charge sharing does not occur.

FIG. 9C schematically shows another example of various waveforms with respect to FIG. 9A. Different from FIG. 9B, v_charge is below the predetermined reference voltage, v_ref at all times. As a result, the corresponding decision signal, out, has a low voltage ("0") at all times. As described above, it may be determined that, in this case, charge sharing occurs.

The semiconductor X-ray detector 100 may be used for phase-contrast X-ray imaging (PCI) (also known as phase-sensitive X-ray imaging). PCI encompasses techniques that form an image of an object at least partially using the phase shift (including the spatial distribution of the phase shift) of an X-ray beam caused by that object. One way to obtain the phase shift is transforming the phase into variations in intensity.

PCI can be combined with tomographic techniques to obtain the 3D-distribution of the real part of the refractive index of the object. PCI is more sensitive to density variations in the object than conventional intensity-based X-ray imaging (e.g., radiography). PCI is especially useful for imaging soft tissues.

According to an embodiment, FIG. 10 schematically shows a system 1900 suitable for PCI. The system 1900 may include at least two X-ray detectors 1910 and 1920. One or both of the two X-ray detectors 1910 is the semiconductor X-ray detector 100 described herein. The X-ray detectors 1910 and 1920 may be spaced apart by a spacer 1930. The spacer 1930 may have very little absorption of the X-ray. For example, the spacer 1930 may have a very small mass attenuation coefficient (e.g., <10 cm$^2$g$^{-1}$, <1 cm$^2$g$^{-1}$, <0.1 cm$^2$g$^{-1}$, or <0.01 cm$^2$g$^{-1}$). The mass attenuation coefficient of the spacer 1930 may be uniform (e.g., variation between every two points in the spacer 1930 less than 5%, less than 1% or less than 0.1%). The spacer 1930 may cause the same amount of changes to the phase of X-ray passing through the spacer 1930. For example, the spacer 1930 may be a gas (e.g., air), a vacuum chamber, may comprise aluminum, beryllium, silicon, or a combination thereof.

The system 1900 can be used to obtain the phase shift of incident X-ray 1950 caused by an object 1960 being imaged. The X-ray detectors 1910 and 1920 can capture two images (i.e., intensity distributions) simultaneously. Because of the X-ray detectors 1910 and 1920 are separated by the spacer 1930, the two images are different distances from the object 1960. The phase may be determined from the two images, for example, using algorithms based on the linearization of the Fresnel diffraction integral.

According to an embodiment, FIG. 11 schematically shows a system 1800 suitable for PCI. The system 1800 comprises the semiconductor X-ray detector 100 described herein. The semiconductor X-ray detector 100 is configured to move to and capture images of an object 1860 exposed to incident X-ray 1850 at different distances from the object 1860. The images may not necessarily be captured simultaneously. The phase may be determined from the images, for example, using algorithms based on the linearization of the Fresnel diffraction integral.

FIG. 12 schematically shows a system comprising the semiconductor X-ray detector 100 described herein. The system may be used for medical imaging such as chest X-ray radiography, abdominal X-ray radiography, etc. The system comprises an X-ray source 1201. X-ray emitted from the X-ray source 1201 penetrates an object 1202 (e.g., a human body part such as chest, limb, abdomen), is attenuated by different degrees by the internal structures of the object 1202 (e.g., bones, muscle, fat and organs, etc.), and is projected to the semiconductor X-ray detector 100. The semiconductor X-ray detector 100 forms an image by detecting the intensity distribution of the X-ray.

FIG. 13 schematically shows a system comprising the semiconductor X-ray detector 100 described herein. The system may be used for medical imaging such as dental X-ray radiography. The system comprises an X-ray source 1301. X-ray emitted from the X-ray source 1301 penetrates an object 1302 that is part of a mammal (e.g., human) mouth. The object 1302 may include a maxilla bone, a palate bone, a tooth, the mandible, or the tongue. The X-ray is attenuated by different degrees by the different structures of the object 1302 and is projected to the semiconductor X-ray detector 100. The semiconductor X-ray detector 100 forms an image by detecting the intensity distribution of the X-ray. Teeth absorb X-ray more than dental caries, infections, periodontal ligament. The dosage of X-ray radiation received by a dental patient is typically small (around 0.150 mSv for a full mouth series).

FIG. 14 schematically shows a cargo scanning or non-intrusive inspection (NII) system comprising the semiconductor X-ray detector 100 described herein. The system may be used for inspecting and identifying goods in transportation systems such as shipping containers, vehicles, ships, luggage, etc. The system comprises an X-ray source 1401. X-ray emitted from the X-ray source 1401 may backscatter from an object 1402 (e.g., shipping containers, vehicles, ships, etc.) and be projected to the semiconductor X-ray detector 100. Different internal structures of the object 1402 may backscatter X-ray differently. The semiconductor X-ray detector 100 forms an image by detecting the intensity distribution of the backscattered X-ray and/or energies of the backscattered X-ray photons.

FIG. 15 schematically shows another cargo scanning or non-intrusive inspection (NII) system comprising the semiconductor X-ray detector 100 described herein. The system may be used for luggage screening at public transportation stations and airports. The system comprises an X-ray source 1501. X-ray emitted from the X-ray source 1501 may penetrate a piece of luggage 1502, be differently attenuated by the contents of the luggage, and projected to the semiconductor X-ray detector 100. The semiconductor X-ray detector 100 forms an image by detecting the intensity distribution of the transmitted X-ray. The system may reveal contents of luggage and identify items forbidden on public transportation, such as firearms, narcotics, edged weapons, flammables.

FIG. 16 schematically shows a full-body scanner system comprising the semiconductor X-ray detector 100 described herein. The full-body scanner system may detect objects on a person's body for security screening purposes, without physically removing clothes or making physical contact.

The full-body scanner system may be able to detect non-metal objects. The full-body scanner system comprises an X-ray source 1601. X-ray emitted from the X-ray source 1601 may backscatter from a human 1602 being screened and objects thereon, and be projected to the semiconductor X-ray detector 100. The objects and the human body may backscatter X-ray differently. The semiconductor X-ray detector 100 forms an image by detecting the intensity distribution of the backscattered X-ray. The semiconductor X-ray detector 100 and the X-ray source 1601 may be configured to scan the human in a linear or rotational direction.

FIG. 17 schematically shows an X-ray computed tomography (X-ray CT) system comprising the semiconductor X-ray detector 100 described herein. The X-ray CT system uses computer-processed X-rays to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The X-ray CT system comprises the semiconductor X-ray detector 100 described herein and an X-ray source 1701. The semiconductor X-ray detector 100 and the X-ray source 1701 may be configured to rotate synchronously along one or more circular or spiral paths.

FIG. 18 schematically shows an electron microscope comprising the semiconductor X-ray detector 100 described herein. The electron microscope comprises an electron source 1801 (also called an electron gun) that is configured to emit electrons. The electron source 1801 may have various emission mechanisms such as thermionic, photocathode, cold emission, or plasmas source. The emitted electrons pass through an electronic optical system 1803, which may be configured to shape, accelerate, or focus the electrons. The electrons then reach a sample 1802 and an image detector may form an image therefrom. The electron microscope may comprise the semiconductor X-ray detector 100 described herein, for performing energy-dispersive X-ray spectroscopy (EDS). EDS is an analytical technique used for the elemental analysis or chemical characterization of a sample. When the electrons incident on a sample, characteristic X-rays may be emitted from the sample. The incident electrons may excite an electron in an inner shell of an atom in the sample, ejecting it from the shell while creating an electron hole where the electron was. An electron from an outer, higher-energy shell then fills the hole, and the difference in energy between the higher-energy shell and the lower energy shell may be released in the form of an X-ray. The number and energy of the X-rays emitted from the sample can be measured by the semiconductor X-ray detector 100.

FIG. 19 schematically shows a radiation dose meter comprising the semiconductor X-ray detector 100 described herein. The radiation dose meter is capable of measuring an average dose rate of a radiation, e.g. X-ray, from a radiation source 1901. The radiation source 1901 may be a volcano 1903 or an atom bomb explosion. The radiation dose meter may include a chamber 1902 that includes air or other gas. X-ray going through a gas will ionize it, producing positive ions and free electrons. An incoming photon will create a number of such ion pairs proportional to its energy. An X-ray detector associated with the radiation dose meter can measure the average dose rate over the gas volume or the number of interacting photons. While the X-ray detector in the non-image application is usually a single pixel detector, the X-ray detector 100 having a plurality of pixels described herein can also be utilized with the capability of managing charge sharing that may occur on neighboring pixels.

FIG. 20 schematically shows an element analyzer comprising the semiconductor X-ray detector 100 described herein. The element analyzer measurer is capable of detecting presence of one or more elements of interest on an object such as a toy. A high-energy beam of charged particles such as electrons or protons, or a beam of X-rays, is directed onto the object. Atoms of the objects are excited and emit X-ray at specific wavelengths that are characteristic of the elements. The X-ray detector 100 receives the emitted X-ray and determines the presence of the elements based on the energy of the emitted X-ray. For example, the X-ray detector 100 may be configured to detect X-ray at wavelengths Pb would emit. If the X-ray detector 100 actually receives X-ray from the object at these wavelengths, it can tell that Pb is present. The semiconductor X-ray detector 100 described here may have other applications such as in an X-ray telescope, X-ray mammography, industrial X-ray defect detection, X-ray microscopy or microradiography, X-ray casting inspection, X-ray non-destructive testing, X-ray weld inspection, X-ray digital subtraction angiography, etc. It may be suitable to use this semiconductor X-ray detector 100 in place of a photographic plate, a photographic film, a PSP plate, an X-ray image intensifier, a scintillator, or another semiconductor X-ray detector.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An apparatus comprising:
    an array of pixels configured to detect X-ray; and
    a controller configured for:
        determining whether charge sharing occurs at a pixel in the array and a neighboring pixel in the array, and
        after determination that the charge sharing occurs, resetting a signal from the pixel without reading the signal;
    wherein determining whether the charge sharing occurs comprises:
        obtaining a first waveform of voltage from the pixel;
        obtaining a second waveform of voltage from the neighboring pixel;
        determining a characteristic associated with the first waveform of voltage and the second waveform of voltage;
        determining whether the charge sharing occurs based on the characteristic;
    wherein the characteristic is, or is a function of, a time difference between a rising or falling edge of the first waveform of voltage and the rising or falling edge of the second waveform of voltage.

2. The apparatus of claim 1, wherein the controller comprises a first D-type flip-flop (DFF) and a second DFF, and wherein the first waveform of voltage is inputted to the first DFF, and the second waveform of voltage is inputted to the second DFF.

3. The apparatus of claim 2, wherein the controller is further configured to generate a first signal based on a first output signal from the first DFF and a second output signal from the second DFF, and wherein the first signal indicates a time difference of a rising edge or falling edge of the first waveform of voltage and a rising edge or falling edge of the second waveform of voltage.

4. The apparatus of claim 3, wherein a signal generated based on the first output signal and the second output signal is fed back as an input to the first DFF and the second DFF.

5. The apparatus of claim 3, wherein the controller further comprises an N-channel field effect transistor (N-FET), a P-channel field effect transistor (P-FET), and a capacitor.

6. The apparatus of claim 5, wherein the controller is further configured to generate a second signal based on the first signal, and wherein a peak value of the second signal is proportional to the time difference of the rising edge or falling edge of the first waveform of voltage and the rising edge or falling edge of the second waveform of voltage.

7. A system comprising the apparatus of claim 1, and an X-ray source or an electron source.

8. A system suitable for phase-contrast X-ray imaging (PCI), the system comprising:
   the apparatus of claim 1;
   a second X-ray detector; and
   a spacer, wherein the apparatus and the second X-ray detector are spaced apart by the spacer.

9. The system of claim 8, wherein the apparatus and the second X-ray detector are configured for respectively capturing an image of an object simultaneously.

10. The system of claim 8, wherein the second X-ray detector is identical to the apparatus.

11. A system suitable for phase-contrast X-ray imaging (PCI), the system comprising the apparatus of claim 1, wherein the apparatus is configured for moving to and capturing images of an object exposed to incident X-ray at different distances from the object.

12. A method comprising:
   determining whether charge sharing occurs at a pixel of an X-ray detector and a neighboring pixel of the X-ray detector; and
   after determination that the charge sharing occurs, resetting a signal from the pixel without reading the signal;
   wherein determining whether the charge sharing occurs comprises:
      obtaining a first waveform of voltage from the pixel;
      obtaining a second waveform of voltage from the neighboring pixel;
      determining a characteristic associated with the first waveform of voltage and the second waveform of voltage;
      determining whether the charge sharing occurs based on the characteristic;
   wherein the characteristic is, or is a function of, a time difference between a rising or falling edge of the first waveform of voltage and the rising or falling edge of the second waveform of voltage.

* * * * *